US006333405B1

(12) United States Patent
Anderson et al.

(10) Patent No.: US 6,333,405 B1
(45) Date of Patent: Dec. 25, 2001

(54) HIGH AFFINITY HUMANIZED ANTI-CEA MONOCLONAL ANTIBODIES

(75) Inventors: W. H. Kerr Anderson, Midland, MI (US); Philip R. Tempest, Cambridge (GB); Frank J. Carr, Balmedie (GB); William J. Harris, Angus (GB); Kathryn Armour, Cambridge (GB)

(73) Assignee: The Dow Chemical Company, Midland, MI (US)

( * ) Notice: Subject to any disclaimer, the term of this patent is extended or adjusted under 35 U.S.C. 154(b) by 0 days.

(21) Appl. No.: 09/672,609

(22) Filed: Sep. 28, 2000

Related U.S. Application Data

(60) Division of application No. 09/025,403, filed on Feb. 18, 1998, which is a continuation-in-part of application No. PCT/US97/19642, filed on Oct. 30, 1997, now abandoned.
(60) Provisional application No. 60/029,694, filed on Oct. 31, 1996, now abandoned.

(51) Int. Cl.[7] .................................................... C07H 21/04
(52) U.S. Cl. .................................. 536/23.53; 530/387.3; 435/320.1
(58) Field of Search ............................. 536/23.1, 23.53, 536/24.1; 530/387.1, 387.3, 388.1, 388.85, 388.8; 424/133.1, 141.1, 156.1, 320.1

(56) References Cited

U.S. PATENT DOCUMENTS

| | | |
|---|---|---|
| 4,816,397 | 3/1989 | Boss et al. . |
| 5,225,539 | 7/1993 | Winter . |
| 5,472,693 | 12/1995 | Gourlie et al. . |

OTHER PUBLICATIONS

Abraham, et al., "Conjugates of COL–1 Monoclonal Antibody and β–D–Galactosidase Can Specifically Kill Tumor Cells by Generation of 5–Fluorouridine from the Prodrug β–D–Galactosyl–5–Fluorouridine", Cell Biophysics, vol. 24/35, pp. 127–133 (1994).
Amit, et al., "Three–Dimensional Structure of an Antigen–Antibody Complex at 2.8 Å Resolution", Science, vol. 233, pp. 747–753 (1986).
Caron, et al., "Biological and Immunological Features of Humanized M195 (Anti–CD33) Monoclonal Antibodies", Cancer Research, vol. 52, pp. 6761–6767 (1992).
Chothia, et al., "Conformations of immunoglobulin hypervariable regions", Nature, vol. 342, pp. 877–883 (1989).
Chothia and Lesk, "Canonical Structures for the Hypervariable Regions of Immunoglobulins", Journal Mol. Biol., vol. 196, pp 901–917 (1987).
Co, et al., "Humanized antibodies for therapy", Nature, vol. 351, pp. 501–502 (1991).
Colman, et al., "Three–dimensional structure of a complex of antibody with influenza virus neuraminidase", Nature, vol. 326, pp. 358–363 (1987).

Fischmann, et al., "Crystallographic Refinement of the Three–dimensional Structure of the FabD1.3–Lysozyme Complex at 2.5–Å Resolution", The Journal of Biological Chemistry, vol. 266, No. 20, pp. 12915–12920 (1991).
Greiner, et al., "Intraperitoneal Administratin of Interferon–Gamma to Carcinoma Patients Enhances Expression of Tumor–Associated Glycoprotein–72 and Carcinoembroyonic Antigen on Malignant Ascites Cells", Journal of Clinical Oncology, vol. 10, No. 5, pp. 735–746 (1992).
Jones, et al., "Replacing the complementarity–determining regions in a human antibody with those from a mouse", Nature, vol. 321, pp. 522–525 (1986).
Morrison and Oi, "Genetically Engineered Antibody Molecules", Advances in Immunology, vol. 44, pp. 65–92 (1989).
Morrison, et al., "Chimeric human antibody molecules: Mouse antigen–binding domains with human constant region domains", Proc. Natl. Acad. Sci. USA, vol. 81, pp. 6851–6855 (1984).
Muraro, et al., "Definition by Monoclonal Antibodies of a Repertoire of Epitopes on Carcinoembryonic Antigen Differentially Expressed in Human Colon Carcinomas versus Normal Adult Tissues", Cancer Research, vol. 45, pp. 5759–5780 (1985).
Ohuchi, et al., "Differential Expression of Carcinoembryonic Antigen in Early Gastric Adenocarcinomas versus Benign Gastric Lesions Defined by Monoclonal Antibodies Reactive With Restricted Antigen Epitopes", Cancer Research, vol. 47, pp. 3565–3571 (1987).
Padlan, "A Possible Procedure for Reducing the Immunogenicity of Antibody Variable Domains While Preserving Their Ligand–Binding Properties", Molecular Immunology, vol. 28, No. 4/5, pp. 489–498 (1991).
Padlan,et al., "Structure of an antibody–antigen complex: Crystal structure of the HyHEL–10–Fab–Iysozyme complex", Proc. Natl. Acad. Sci. USA, vol. 86, pp. 5938–5942 (1989).
Padlan, "Anatomy of the Antibody Molecule", Molecular Immunology, vol. 31, No. 3, pp. 169–217 (1994).
Page, et al., "High Level Expression of the Humanized Monoclonal Antibody Campath–1H in Chinese Hamster Ovary Cells", Bio/Technology, vol. 9, pp. 64–68 (1991).

(List continued on next page.)

Primary Examiner—Sheela Huff
Assistant Examiner—Larry R. Helms
(74) Attorney, Agent, or Firm—Mark S. Scott; Karen L. Kimble

(57) ABSTRACT

Novel humanized monoclonal antibodies, fragments or derivatives thereof which specifically bind carcinoembryonic antigen (CEA) are provided as well as methods for their manufacture. These humanized antibodies are useful in the treatment of cancers which express CEA as well as for diagnostic purposes, e.g., for in vivo imaging of tumors or cancer cells which express CEA.

5 Claims, 18 Drawing Sheets

OTHER PUBLICATIONS

Queen, et al., "A humanized antibody that binds to the interleukin 2 receptor", Proc. Natl. Acad. Sci. USA, vol. 86, pp. 10029–10033 (1989).

Riechmann, et al., "Reshaping human antibodies for therapy", Nature, vol. 332, pp. 323–327 (1988).

Robbins, et al., "Definition of the Expression of the Human Carcinoembryonic Antigen and Non–Specific Cross–Reacting Antigen in Human Breast and Lung Carcinomas", Int. Journal Cancer, vol. 53, pp. 892–897 (1993).

Sheriff, et al., "Three–dimensional structure of an antibody–antigen complex", Proc. Natl. Acad. Sci. USA, vol. 84, pp. 8075–8079 (1987).

Siler, et al., "Therapeutic Efficacy of a High–Affinity Anti-carcinoembryonic Antigen Monoclonal Antibody (COL–1)", Biotechnology Therapeutics, vol. 4, No. 3–4, pp. 163–181 (1993).

Singer, et al., "Optimal Humanization of 1B4, an Anti–CD18 Murine Monoclonal Antibody, Is Achieved by Correct Choice of Human V–Region Framework Sequences", The Journal of Immunology, vol. 150, No. 7, pp. 2844–2857 (1993).

Tempest, et al., "Reshaping a Human Monoclonal Antibody to Inhibit Human Respiratory Syncytial Virus Infection In Vivo", Bio/Technology, vol. 9, pp. 266–271 (1991).

Tramontano, et al., "Framework Residue 71 is a Major Determinant of the Position and Conformation of the Second Hypervariable Region in the $V_H$ Domains of Immunoglobulins", J. Mol. Biol., vol. 215, pp. 175–182 (1990).

Tulip, et al., "Refined Crystal Structure of the Influenze Virus N9 Neuraminidase–NC41 Fab Complex", J. Mol. Biol., vol. 227, pp. 122–148 (1992).

Verhoeyen, et al., "Reshaping Human Antibodies: Grafting an Antilysozyme Activity", Science, vol. 239, pp. 1534–1536 (1988).

Yu, et al., "Phase I Trial of Iodine 131—Labeled COL–1 in Patients with Gastrointestinal Malignancies: Influence of Serum Carcinoembryonic Antigen and Tumor Bulk on Pharmacokinetics", Journal of Clinical Oncology, vol. 14, No. 6, pp. 1798–1809 (1996).

FIG. 1

```
                    10         20          30         40         50
                    v          v     A     v          v          v
COL1MuVH    EVQLQQSGAELVRSGASVKMSCTASGFNIKDYYMHWVKQRPEQGLEWIGWI
NEWMVH      QVQLQESGPGLVRPSQTLSLTCTVSGFNIKDYYMHWVRQPPGRGLEWIGWI
COL1NMVH    QVQLQESGPGLVRPSQTLSLTCTVSGFNIKDYYMHWVRQPPGRGLEWIGWI
                    ^          ^    ↑↑↑↑   ^          ^          ^
                    10         20          30         40         50

60         70          80         90         100
                    v          v T    S TAY           v          v
COL1MuVH    DPENGDTEYAPKFQGKATMTTDTSSNTAYLQLSSLTSEDTAVYYCNTRGLS
NEWMVH      DPEN    YAPKFQGRVTMLVDTSKNQFSLRLSSVTAADTAVY
COL1NMVH    DPENGDTEYAPKFQGRVTMLVDTSKNQFSLRLSSVTAADTAVYYCNTRGLS
                    ^          ^          ^          ^      ↑↑  ^
                    60         70         80         90         100

110        120
                    v          v
COL1MuVH    TMITTRWFFDVWGAGTTVAVSS
NEWMVH                          VTVSS
COL1NMVH    TMITTRWFFDVWGQGSLVTVSS
                    ^          ^
                    110        120
```

FIG. 2

```
                    10        20        30        40        50
            VL      v         v         v         v         v
COL1MuVK    DIVLTQSPASLTVSLGLRATISCRASKSVSASGYSYMHWYQQRPGQPPKLL
REIVI       DIQLTQSPSSLSASVGDRVTITCR         GYSYMHWYQQKPGKAPKLL
COL1REVK    DIQMTQSPSSLSASVGDRVTITCRASKSVSASGYSYMHWYQQTPGKAPKLL
                    ^         ^         ^         ^         ^
                    10        20        30        40        50

60        70        80        90        100
                    v         v    F    v         v         v
COL1MuVK    IYLASNLQSGVPARFSGSGSGTDFTLNIHPVEEEDAATYYCQHSRELPTFG
REIVK       IY        SGVPSRFSGSGSGTDFTFTISSLQPEDIATYYCQ     TFG
COL1REVK    IYLASNLQSGVPSRFSGSGSGTDYTFTISSLQPEDIATYYCQHSRELPTFG
                    ^         ^         ^         ^         ^
                    60        70        80        90        100

110
                    v
COL1MuVK    GGTKLEIK
REIVK       QGTK
COL1REVK    QGTKLQIT
                    ^
                    110
```

Mammalian Cell Vectors for the Expression of Humanized V Regions

Binding of COL1 antibodies to CEA measured by ELISA

+ HuVH/HuVKVL
○ MuVH/MuVK
□ HuVHS/HuVKVL
♦ Irrelevant HumAb

Binding of COL1 antibodies to CEA measured by ELISA

Binding of COL1 antibodies to CEA measured by ELISA

○ MuVH/MuVK
× HuVHSTAY/HuVK
♦ HuVHSTAY/HuVKVL
⊠ Irrelevant HumAb

Binding of COL1 antibodies to CEA measured by ELISA

○ MuVH/MuVK
+ HuVH/HuVK
□ HuVHSTAY/HuVKVL

FIG. 13

```
              10        20        30        40        50
              v         v         v         v         v
COL1NMVH   QVQLQESGPGLVRPSQTLSLTCTVSGFNIKDYYMHWVRQPPGRGLEWIGWI
              ^         ^         ^         ^         ^
              10        20        30        40        50

60        70        80        90        100
              v         v         v         v         v
COL1NMVH   DPENGDTEYAPKFQGRVTMLVDTSSNTAYLRLSSVTAADTAVYYCNTRGLS
              ^         ^         ^         ^         ^
              60        70        80        90        100

110       120
              v         v
COL1NMVH   TMITTRWFFDVWGQGSLVTVSS
              ^         ^
              110       120
```

FIG. 14

```
             10          20          30          40          50
              v           v           v           v           v
COL1REVK    DIVLTQSPSSLSASVGDRVTITCRASKSVSASGYSYMHWYQQTPGKAPKLL
              ^           ^           ^           ^           ^
             10          20          30          40          50

60          70          80          90         100
              v           v           v           v           v
COL1REVK    IYLASNLQSGVPSRFSGSGSGTDYTFTISSLQPEDIATYYCQHSRELPTFG
              ^           ^           ^           ^           ^
             60          70          80          90         100

110
              v
COL1REVK    QGTKLQIT
              ^
            110
```

FIG. 15

```
          270             280             290             300
           v               v               v               v
CAG GTC CAA CTG CAG GAG AGC GGT CCA GGT CTT GTG AGA CCT AGC CAG
GTC CAG GTT GAC GTC CTC TCG CCA GGT CCA GAA CAC TCT GGA TCG GTC 310         320         330         340         350
       v           v           v           v           v
ACC CTG AGC CTG ACC TGC ACC GTG TCT GGC TTC AAC ATT AAA GAC TAC
TGG GAC TCG GAC TGG ACG TGG CAC AGA CCG AAG TTG TAA TTT CTG ATG 360         370         380         390         400
       v           v           v           v           v
TAT ATG CAC TGG GTG AGA CAG CCA CCT GGA CGA GGT CTT GAG TGG ATT
ATA TAC GTG ACC CAC TCT GTC GGT GGA CCT GCT CCA GAA CTC ACC TAA 410         420             440         450
       v           v               v           v
GGA TGG ATT GAT CCT GAG AAT        TAT GCC CCG AAG TTC CAG GGC
CCT ACC TAA CTA GGA CTC TTA...  ...ATA CGG GGC TTC AAG GTC CCG 460         470         480         490         500
       v           v           v           v           v
AGA GTG ACA ATG CTG GTA GAC ACC AGC AAG AAC CAG TTC AGC CTG AGA
TCT CAC TGT TAC GAC CAT CTG TGG TCG TTC TTG GTC AAG TCG GAC TCT 510         520         530         540
       v           v           v           v
CTC AGC AGC GTG ACA GCC GCC GAC ACC GCG GTC TAT         GTC ACC
GAG TCG TCG CAC TGT CGG CGG CTG TGG CGC CAG ATA...   ...CAG TGG 600
 v
GTC TCC TCA
CAG AGG AGT
```

FIG. 16

```
        270             280             290             300
         v               v               v               v
CAG GTC CAA CTG CAG GAG AGC GGT CCA GGT CTT GTG AGA CCT AGC CAG
GTC CAG GTT GAC GTC CTC TCG CCA GGT CCA GAA CAC TCT GGA TCG GTC 310             320             330             340             350
     v               v               v               v               v
ACC CTG AGC CTG ACC TGC ACC GTG TCT GGC TTC AAC ATT AAA|GAC TAC
TGG GAC TCG GAC TGG ACG TGG CAC AGA CCG AAG TTG TAA TTT|CTG ATG 360             370             380             390             400
       v               v               v               v               v
TAT ATG CAC|TGG GTG AGA CAG CCA CCT GGA CGA GGT CTT GAG TGG ATT
ATA TAC GTG|ACC CAC TCT GTC GGT GGA CCT GCT CCA GAA CTC ACC TAA 410             420             430             440             450
         v               v               v               v               v
GGA|TGG ATT GAT CCT GAG AAT GGT GAT ACT GAA TAT GCC CCG AAG TTC
CCT|ACC TAA CTA GGA CTC TTA CCA CTA TGA CTT ATA CGG GGC TTC AAG 460             470             480             490             500
           v               v               v               v               v
CAG GGC|AGA GTG ACA ATG CTG GTA GAC ACC AGC AAG AAC CAG TTC AGC
GTC CCG|TCT CAC TGT TAC GAC CAT CTG TGG TCG TTC TTG GTC AAG TCG 510             520             530             540
               v               v               v               v
CTG AGA CTC AGC AGC GTG ACA GCC GCC GAC ACC GCG GTC TAT TAC TGT
GAC TCT GAG TCG TCG CAC TGT CGG CGG CTG TGG CGC CAG ATA 550             560             570             580             590
 v               v               v               v               v
AAT ACA|CGG GGT CTA TCT ACT ATG ATT ACG ACG CGT TGG TTC TTC GAT
TTA TGT|GCC CCA GAT AGA TGA TAC TAA TGC TGC GCA ACC AAG AAG CTA 600             610             620             630
         v               v               v               v
GTC|TGG GGC CAA GGG TCC TTG GTC ACC GTC TCC TCA
CAG|ACC CCG GTT CCC AGG AAC CAG TGG CAG AGG AGT
```

FIG. 17

```
          270             280             290                 300
           v               v               v                   v
GAC ATC CAR CTG ACC CAG AGC CCA AGC AGC CTG AGC GCC AGC GTG GGT 310             320             330             360             370
 v               v               v               v               v
GAC AGA GTG ACC ATC ACC TGT AGG...    ...GGC TAT AGT TAT ATG CAC 380             390             400             410
       v               v               v               v
TGG TAC CAG CAG ACG CCA GGT AAG GCT CCA AAG CTG CTG ATC TAC...

440             450             460             470             480
       v               v               v               v               v
...TCT GGT GTG CCA AGC AGA TTC AGC GGT AGC GGT AGC GGT ACC GAC 490             500             510             520             530
           v               v               v               v               v
TTY ACC TTC ACC ATC AGC AGC CTC CAG CCA GAG GAC ATC GCC ACC TAC 560             570
                 v               v
TAC TGC CAG...    ...ACG TTC GGC CAA GGG ACC AAG
```

FIG. 18

```
           270              280              290              300
            v                v                v                v
GAC ATC CAR ATG ACC CAG AGC CCA AGC AGC CTG AGC GCC AGC GTG GGT 310              320              330              340              350
   v                v                v                v                v
GAC AGA GTG ACC ATC ACC TGT|AGG GCC AGC AAA AGT GTC AGT GCA TCT 360              370              380              390              400
        v                v                v                v                v
   GGC TAT AGT TAT ATG CAC|TGG TAC CAG CAG ACG CCA GGT AAG GCT CCA 410              420              430              440              450
           v                v                v                v                v
      AAG CTG CTG ATC TAC|CTT GCA TCC AAC CTA CAA TCT|GGT GTG CCA AGC 460              470              480              490              500
             v                v                v                v                v
        AGA TTC AGC GGT AGC GGT AGC GGT ACC GAC TAC ACC TTC ACC ATC AGC 510              520              530              540
               v                v                v                v
          AGC CTC CAG CCA GAG GAC ATC GCC ACC TAC TAC TGC|CAG CAC AGT AGG 560              570              580              590
                 v                v                v                v
            GAG CTT CCT ACG|TTC GGC CAA GGG ACC AAG CTG CAA ATC ACA
```

HIGH AFFINITY HUMANIZED ANTI-CEA MONOCLONAL ANTIBODIES

CROSS-REFERENCE TO RELATED APPLICATIONS

The present Application is a Division of copending U.S. patent application Ser. No. 09/025,403, filed Feb. 18, 1998, which is a Continuation-in-Part of International Application Serial No. PCT/US97/19642, filed Oct. 30, 1997 designating the United States, now abandoned, which is a Continuation-in-Part of U.S. Provisional Patent Application Serial No. 60/029,694, filed Oct. 31, 1996, now abandoned.

FIELD OF THE INVENTION

The present invention relates to humanized monoclonal antibodies and fragments or derivatives thereof which specifically bind carcinoembryonic antigen (CEA), which is an antigen expressed by various human carcinomas including breast, lung, and gastrointestinal carcinomas such as stomach and colon cancers. More specifically, the present invention relates to humanized monoclonal antibodies and humanized antibody fragments and derivatives thereof which are derived from murine monoclonal antibody COL-1, a high affinity anti-CEA antibody. The present invention further relates to methods for producing such humanized monoclonal antibodies specific to CEA, pharmaceutical and diagnostic compositions containing such humanized monoclonal antibodies, and methods of use thereof for the treatment or diagnosis of cancer.

BACKGROUND OF THE INVENTION

The identification of antigens expressed by tumor cells and the preparation of monoclonal antibodies which specifically bind such antigens is well known in the art. Anti-tumor monoclonal antibodies exhibit potential application as both therapeutic and diagnostic agents. Such monoclonal antibodies have potential application as diagnostic agents because they specifically bind tumor antigens and thereby can detect the presence of tumor cells or tumor antigen in an analyte. For example, use of monoclonal antibodies which bind tumor antigens for in vitro and in vivo imaging of tumor cells or tumors using a labeled form of such a monoclonal antibody is conventional in the art.

Moreover, monoclonal antibodies which bind tumor antigens have well known application as therapeutic agents. The usage of monoclonal antibodies themselves as therapeutic agents, or as conjugates wherein the monoclonal antibody is directly or indirectly attached to an effector moiety, e.g., a drug, cytokine, cytotoxin, etc., is well known.

Essentially, if the monoclonal antibody is attached to an effector moiety, then the monoclonal antibody functions as a targeting moiety, i.e. it directs the effector moiety (which typically possesses therapeutic activity) to the antibody's target, e.g., a tumor which expresses the antigen bound by the monoclonal antibody. In contrast, when the monoclonal antibody itself operates as a therapeutic agent, the antibody functions both as a targeting moiety—i.e. it will specifically bind a cell which expresses the antigen—and as an effector which mediates therapeutic activity, typically tumor cell lysis. A monoclonal antibody may possess one or more of such effector functions, which include, e.g., antibody-dependent cellular cytotoxicity (ADCC) and complement dependent cytotoxicity (CDC), among others; these functions are effected by the portion of the antibody molecule generally referred to in the literature as the Fc portion.

One specific tumor antigen to which various monoclonal antibodies have been produced is the carcinoembryonic antigen (CEA). CEA is an antigen complex having a molecular weight of about 180,000 D, which is expressed by numerous carcinomas including gastrointestinal carcinomas, colorectal carcinomas, breast carcinomas, ovarian carcinomas, and lung carcinomas. See, e.g., Robbins et al., *Int'l J. Cancer*, 53(6):892–897 (1993); Greiner et al., *J. Clin. Oncol.*, 10(5):735–746 (1992); Obuchi et al., *Cancer Res.*, 47(13):3565–3571 (1987); Muraro et al., *Cancer Res.*, 45(11 Pt. 2):5769–5780 (1985).

The use of monoclonal antibodies to detect various, specific CEA epitopes differentially expressed on human carcinomas has been reported in the literature. See, e.g., Obuchi et al., *Cancer Res.*, 47(13):3565–3571 (1987); Muraro et al., *Cancer Res.*, 45(11 Pt. 2):5769–5780 (1985).

In particular, Muraro et al. (id.) report generation of monoclonal antibodies designated COL-1 through COL-15, which exhibit a strong, selective reactivity for human colon carcinomas versus normal adult tissues. These antibodies react with distinct, restricted epitopes on CEA. Of these antibodies, the COL-1 antibody has been the focus of considerable attention because of its high affinity for CEA ($1.4 \times 10^9$ $M^{-1}$) and also because it comprises no detectable reactivity for CEA-related antigens such as the nonspecific cross-treating antigen (NCA) and the normal fecal antigen (NFA). Robbins et al., *Int'l J. Canc.*, 53(6):892–897 (1993).

Because of its binding properties, COL-1 is currently being evaluated for use as a therapeutic agent. For example, Siler et al. (*Biotech. Ther.*, 4(3–4):163–181 (1993)) report the administration of $^{131}$I-labeled COL-1 to LS-M4T human colon carcinoma xenograft-containing athymic mice. They report that this treatment resulted in reduction of the rate of tumor growth, within little or no toxicity, and that their results demonstrate the potential therapeutic efficacy of radiolabeled COL-1 in clinical trials. Also, Yu et al. (*J. Clin. Oncol.*, 14(6):1798–1809 (1996)) report that $^{131}$I-labeled COL-1 is now in phase 1 clinical trials in patients having gastrointestinal malignancies. They further indicate that the antibody conjugate is well tolerated, except for some hematologic toxicity. In addition, the use of conjugates of COL-1 and $\beta$-galactosidase has been shown to specifically kill in vitro tumor cells from a variety of tumor cell lines. Abraham et al., *Cell Biophys.*, 24–25:127–133 (1994).

However, while murine antibodies, such as COL-1 and other anti-CEA murine antibodies, have applicability as therapeutic agents in humans, they are disadvantageous in some respects. Specifically, because murine antibodies are of foreign species origin, they may be immunogenic in humans. This may result in a neutralizing antibody response—a human anti-murine antibody (HAMA) response—which is particularly problematic if the antibodies are desired to be administered repeatedly, e.g., for treatment of a chronic or recurrent disease condition. This is a significant drawback, as some cancer treatments are effected over a prolonged time period, e.g., over several years or longer. Also, because these antibody molecules contain murine constant domains they may not exhibit human effector functions.

In an effort to eliminate or reduce such problems, chimeric antibodies have been disclosed. Chimeric antibodies contain portions of two different antibodies, typically of two different species. Generally, such antibodies contain human constant regions attached to variable regions from another species, typically murine variable regions. For example, some mouse/human chimeric antibodies have been reported which exhibit binding characteristics of the parental mouse antibody and effector functions associated with the human constant region. See, e.g., U.S. Pat. No. 4,816,567 to Cabilly et al.; U.S. Pat. No. 4,978,745 to Shoemaker et al.; U.S. Pat. No. 4,975,369 to Beavers et al.; and U.S. Pat. No. 4,816,397 to Boss et al. Generally, these chimeric antibodies are constructed by preparing a genomic gene library from DNA extracted from pre-existing murine hybridomas. Nishimura et al., Cancer Res., 47:999 (1987). The library is then screened for variable region genes from both heavy and light chains exhibiting the correct antibody fragment rearrangement patterns. Alternatively, cDNA libraries are prepared from RNA extracted from the hybridomas and then screened, or the variable regions are obtained by polymerase chain reaction. The cloned variable region genes are then ligated into an expression vector containing cloned cassettes of the appropriate heavy or light chain human constant region gene. The chimeric genes are then expressed in a cell line of choice, usually a murine myeloma line. Such chimeric antibodies have been used in human therapy.

Moreover, the production of a chimeric mouse antihuman antibody derived from COL-1, which specifically binds CEA, has been reported. See e.g., U.S. Pat. No. 5,472,693 to Gourlie et al. (owned by The Dow Chemical Company).

Also, Morrison et al. report the preparation of several anti-tumor chimeric monoclonal antibodies, in *Important Advances in Oncology, Recombinant Chimeric Monoclonal Antibodies*, pp. 3–18 (S. A. Rosenberg, ed., 1990) (J. B. Lippincott, Philadelphia, Pa.). Results of clinical trials with chimeric cMAb-17-1A in patients with metastatic colorectal carcinoma now show that this antibody has a 6-fold longer circulation time and significantly reduced immunogenicity as compared to the murine monoclonal antibody from which it was derived. LoBuglio et al., *Proc. Natl. Acad. Sci. USA*, 86:4220–4224 (1989); Meredith et al., *J. Nucl. Med.*, 32:1162–1168 (1991).

However, while such chimerized monoclonal antibodies typically exhibit lesser immunogenicity, they are still potentially immunogenic in humans because they contain murine variable sequences which may elicit antibody responses. Thus, there is the possibility that these chimeric antibodies may elicit an anti-idiotypic response if administered to patients. Saleh et al., *Cancer Immunol. Immunother.*, 32:185–190 (1990).

Because of the immunogenicity of chimeric antibodies, methods have been developed recently for the production of "humanized" antibodies. Ideally, "humanization" results in an antibody that is less immunogenic, with complete retention of the antigen-binding properties of the original molecule. In order to retain all the antigen-binding properties of the original antibody, the structure of its combining-site has to be faithfully reproduced in the "humanized" version. This can potentially be achieved by transplanting the combining site of the nonhuman antibody onto a human framework, either: (a) by grafting only the nonhuman complementarity determining regions (CDRs) onto human framework regions (FRs) and constant regions, with or without retention of critical framework residues (see, Jones et al., *Nature*, 321:522 (1986) and Verhoeyen et al., *Science*, 239:1539 (1988); or (b) by transplanting the entire nonhuman variable domains (to preserve ligand-binding properties) and also "cloaking" them with a human-like surface through judicious replacement of exposed residues (in order to reduce antigenicity) (see, Padlan, *Molec. Immunol.*, 28:489 (1991)).

Essentially, humanization by CDR-grafting involves transplanting only the CDRs onto human framework and constant regions. Theoretically, this should substantially eliminate immunogenicity (except if allotypic or idiotypic differences exist). Jones et al., *Nature*, 321:522–525 (1986); Verhoeyen et al., *Science*, 239:1534–1536 (1988), Riechmann et al., *Nature*, 332:323–327 (1988). However, CDR-grafting by itself may not yield the desired result. Rather, it has been reported that some framework residues of the original antibody may also need to be preserved in order to preserve antigen binding activity. Riechmann et al., *Nature*, 332:323–327 (1988); Queen et al., *Proc. Natl. Acad Sci. USA*, 86:10023–10029; Tempest et al., *Biol. Technology*, 9:266–271 (1991); Co et al., *Nature*, 351:501–502 (1991).

As discussed above, in order to preserve the antigen-binding properties of the original antibody, the structure of its combining site must be faithfully reproduced in the humanized molecule. X-ray crystallographic studies have shown that the antibody combining site is built primarily from CDR residues, although some neighboring framework residues have been found to be involved in antigen binding. Amit et al., *Science*, 233:747–753 (1986); Colman et al., *Nature*, 326:358–363 (1987); Sheriff et al., *Proc. Natl. Acad. Sci. USA*, 84:8075–8079 (1987); Padlan et al., *Proc. Natl. Acad. Sci. USA*, 86:5938–5942 (1989); Fischmann et al., *J. Biol. Chem.*, 266:12915–12920 (1991); Tulip et al., *J. Molec. Biol.*, 227:122–148 (1992). It has also been found that the structures of the CDR loops are significantly influenced by surrounding framework structures. Chothia et al., *J. Molec. Biol.*, 196:901–917 (1987); Chothia et al., *Nature*, 342:877–883 (1989); Tramomonteno et al., *J. Molec. Biol.*, 215:175–182(1990).

In addition to the effect of the framework residues on the CDRs, small but significant differences from the relative disposition of the variable light chain ($V_L$) and variable heavy ($V_H$) domains have been noted (Colman et al., *Nature*, 326:358–363 (1987)) and those differences are ostensibly due to variations in the residues involved in the interdomain contact (Padlan et al., *Molec. Immunol.*, 31:169–217 (1994)).

Furthermore, structural studies on the effect of the mutation of interior residues, in which changes in side chain volume are involved, have shown that the resulting local deformations are accommodated by shifts in side chain positions that are propagated to distant parts of the molecular interior. This suggests that during humanization the interior residues in the variable domains and in the interface between these domains, or at least the interior volumes, should also be maintained; a humanization protocol in which an interior residue is replaced by one of different properties, such as size, charge, or hydrophobicity, could result in a significant modification of the antigen combining-site structure. One method of potentially identifying the framework residues which need to be preserved is by computer modeling. Alternatively, critical framework residues may potentially be identified by comparing known antibody combining site structures. Padlan, *Molec. Immun.*, 31(3):169–217 (1994).

The residues which potentially affect antigen binding fall into several groups. The first group comprises residues that are contiguous with the combining site surface and which could therefore make direct contact with antigens. These residues include the amino-terminal residues and those adjacent to the CDRs. The second group includes residues that could alter the structure or relative alignment of the CDRs by contacting either the CDRs or the opposite chains. The third group comprises amino acids with buried side chains that could influence the structural integrity of the variable domains. The residues in these groups are usually found in the same positions (id.) according to the adopted numbering system. See Kabat et al., *Sequences of Proteins of Immunological Interest*, NIH Pub. No. 91-3242 (5th ed., 1991) (U.S. Dept. Health & Human Services, Bethesda, Md.) and Genbank.

Given these effects of changes in amino acid residues, although humanized antibodies are desirable because of their potential low immunogenicity in humans, their production is unpredictable. For example, sequence modification of antibodies may result in substantial or even total loss of antigen binding affinity, or loss of binding specificity. Alternatively, "humanized antibodies" may still exhibit immunogenicity in humans, irrespective of sequence modification.

Thus, there still exists a significant need in the art for novel humanized antibodies to desired antigens. More specifically, there exists a need in the art for humanized antibodies specific to CEA, because of their potential as improved immunotherapeutic and immunodiagnostic agents for treatment and diagnosis of cancers expressing CEA, e.g., gastrointestinal and colorectal cancers, breast cancers, lung cancers, and ovarian cancers, among others.

OBJECTS OF THE INVENTION

Toward this end, it is an object of the invention to provide humanized antibodies which are specific to human carcinoembryonic antigen (CEA), i.e. anti-CEA ("αCEA") antibodies. More specifically, it is an object of the invention to provide humanized antibodies derived from murine αCEA antibodies and in particular from COL-1, a specific murine antibody of the IgG2a isotype having high affinity for CEA.

It is also an object of the invention to provide pharmaceutical compositions containing humanized αCEA antibodies. It is a more specific object of the invention to provide pharmaceutical compositions containing humanized antibodies derived from the high affinity murine αCEA antibody, COL-1.

It is another specific object of the invention to provide methods of using humanized αCEA antibodies for treatment of cancers which express CEA, in particular breast, lung, ovarian, gastrointestinal, and colorectal cancers, among others.

It is another object of the invention to provide immunodiagnostic compositions for detecting cancer cells, the compositions containing a humanized αCEA antibody, preferably derived from COL-1, which antibody is in labeled or unlabeled form. It is another object of the invention to provide a method of immunodiagnosis of cancer using compositions which contain a humanized αCEA antibody, preferably derived from COL-1, which is in labeled or unlabeled form.

It is still another object of the invention to provide nucleic acid sequences which encode humanized αCEA antibodies or fragments thereof. It is a more specific object of the invention to provide nucleic acid sequences which encode humanized antibodies derived from the high affinity murine αCEA antibody, COL-1. It is another object of the invention to provide vectors which provide for the expression of humanized αCEA antibodies, in particular humanized antibodies derived from the high affinity murine αCEA antibody, COL-1.

BRIEF DESCRIPTION OF THE FIGURES

FIG. 1 contains an alignment of the amino acid sequences of murine COL-1 $V_H$(COL1MuVH) (SEQ ID NO:1), a NEWM FR template (SEQ ID NO:2), and a humanized NEWM-based $V_H$ (COL1NMVH or "HuVH") (SEQ ID NO:3). The CDRs are boxed. Murine FR residues retained in the various humanized VHs exemplified herein are indicated by the symbols (↑), (A), (T), (S), (T), (A), and (Y), according to the table below.

| COL1NMVH Version | * | Murine Residues Retained at Position | | | | |
|---|---|---|---|---|---|---|
| | | 24 | 72 | 76 | 78 | 79 | 80 |
| HuVH (SEQ ID NO: 3) | ↑ | | | | | | |
| HuVHA (SEQ ID NO: 4) | ↑ | A | | | | | |
| HuVHAT (SEQ ID NO: 5) | ↑ | A | | | T | | |
| HuVHAA (SEQ ID NO: 6) | ↑ | A | | | | A | |
| HuVHAY (SEQ ID NO: 7) | ↑ | A | | | | | Y |
| HuVHATAY (SEQ ID NO: 8) | ↑ | A | | | T | A | Y |
| HuVHASTAY (SEQ ID NO: 9) | ↑ | A | | S | T | A | Y |
| HuVHT (SEQ ID NO: 10) | ↑ | | T | | | | |
| HuVHS (SEQ ID NO: 11) | ↑ | | | S | | | |
| HuVHSTAY (SEQ ID NO: 12) | ↑ | | | S | T | A | Y |

(* -- Retained murine residues indicated by the symbol (↑) are F-27, N-28, I-29, K-30, N-97, and T-98.) HuVHSTAY is the version of COL1NMVH expressed from the deposited cell line, ATCC CRL-12208.

FIG. 2 contains an alignment of the amino acid sequences of murine COL-1 $V_K$ (COL1MuVK or "HuVK"), an REI FR template (SEQ ID NO:14), and a humanized REI-based $V_K$ (COL1REVK or HuKVIC)(SEQ ID NO:15). The CDRs are boxed. The murine FR residues retained in the humanized sequence are indicated by the symbols: (F) for HuVKF (SEQ ID NO:17), and (V) and (L) for HuVKVL. HuVKVL (SEQ ID NO:16) is the version of COL1REVK expressed from the deposited cell line, ATCC CRL-12208.

Figure 3:
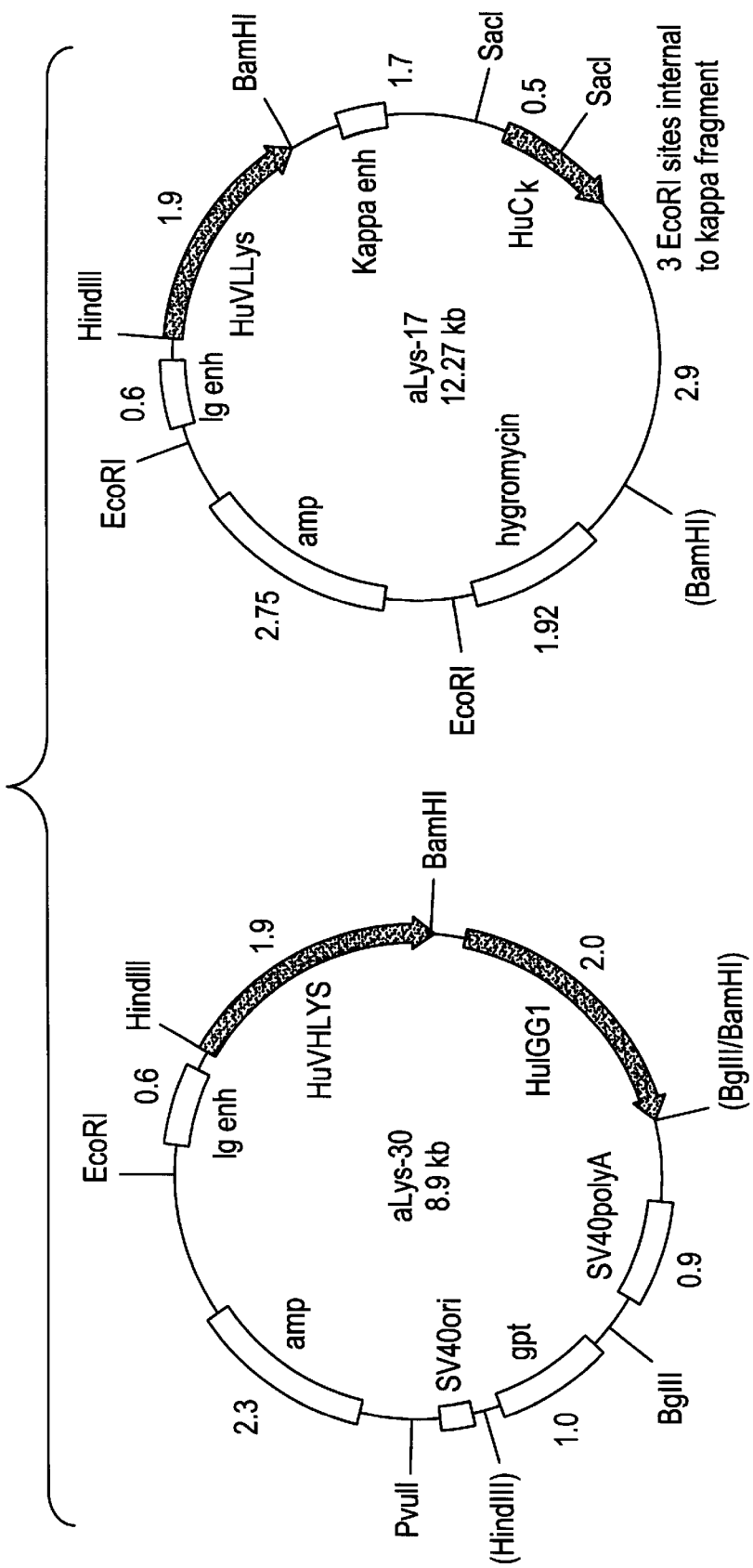

FIG. 3 shows the IgG1 expression vectors used to express the subject humanized antibodies in NSO myeloma cells.

Figure 4:
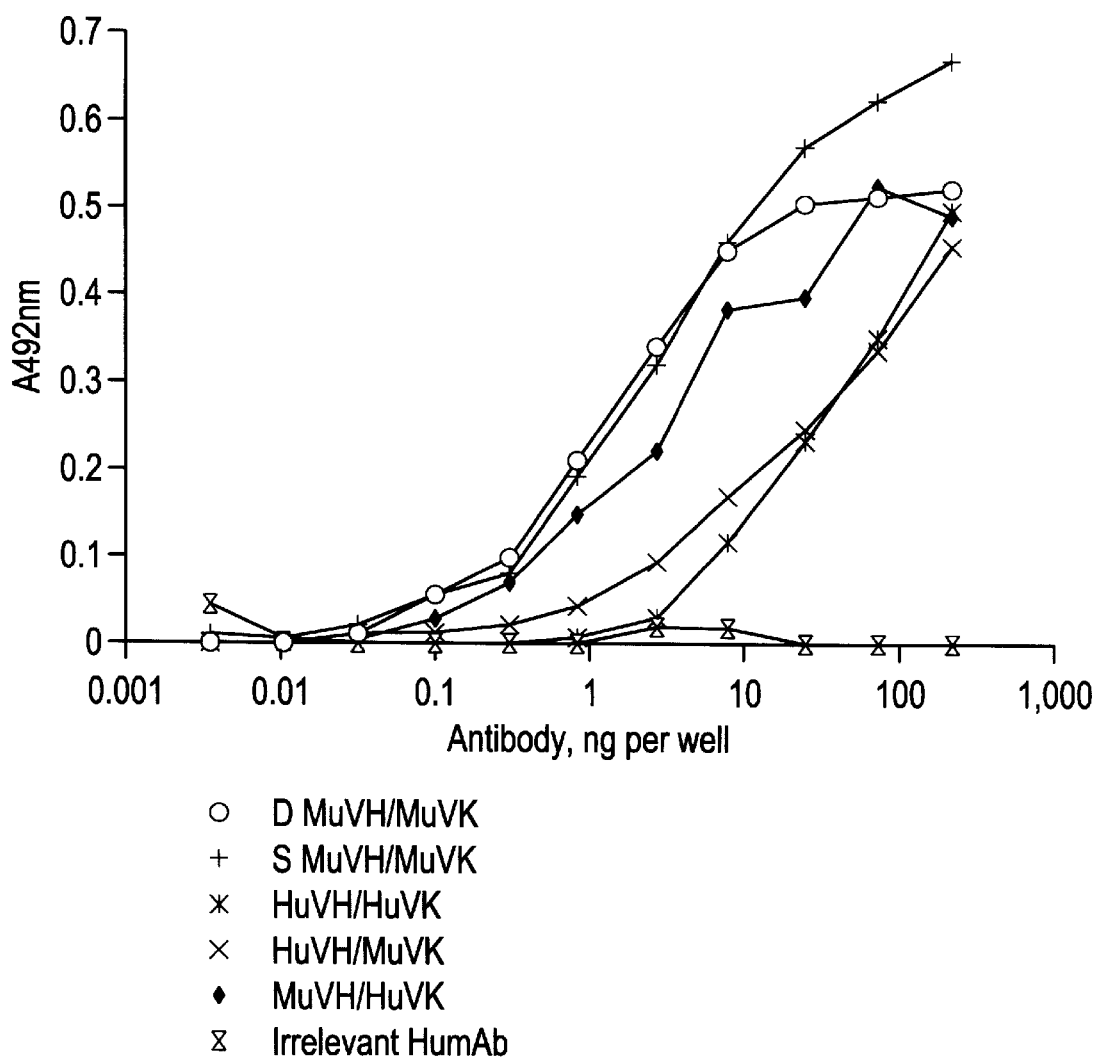

FIG. 4 shows binding of different COL-1 antibodies to CEA, as measured by an ELISA assay.

Figure 5:
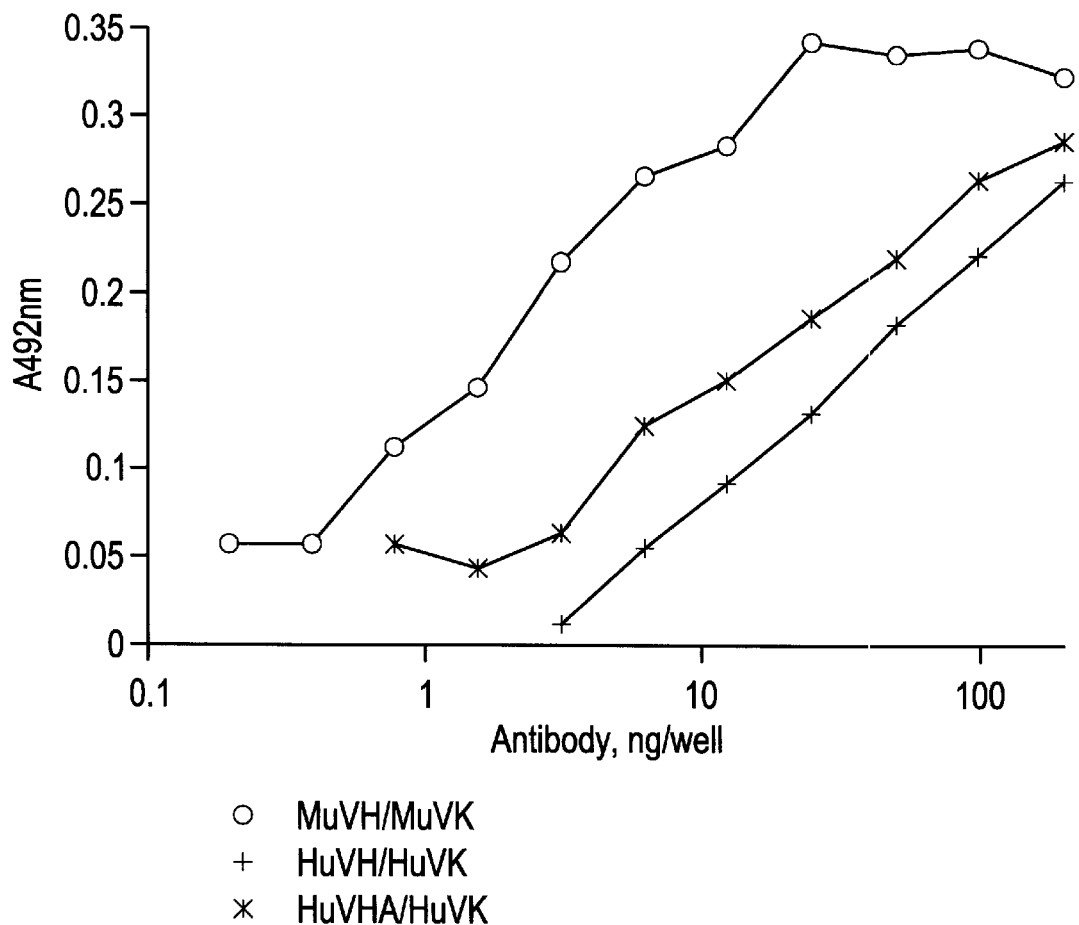

FIG. 5 contains results of ELISA assays with COL-1 antibodies including those produced according to the invention.

Figure 6:
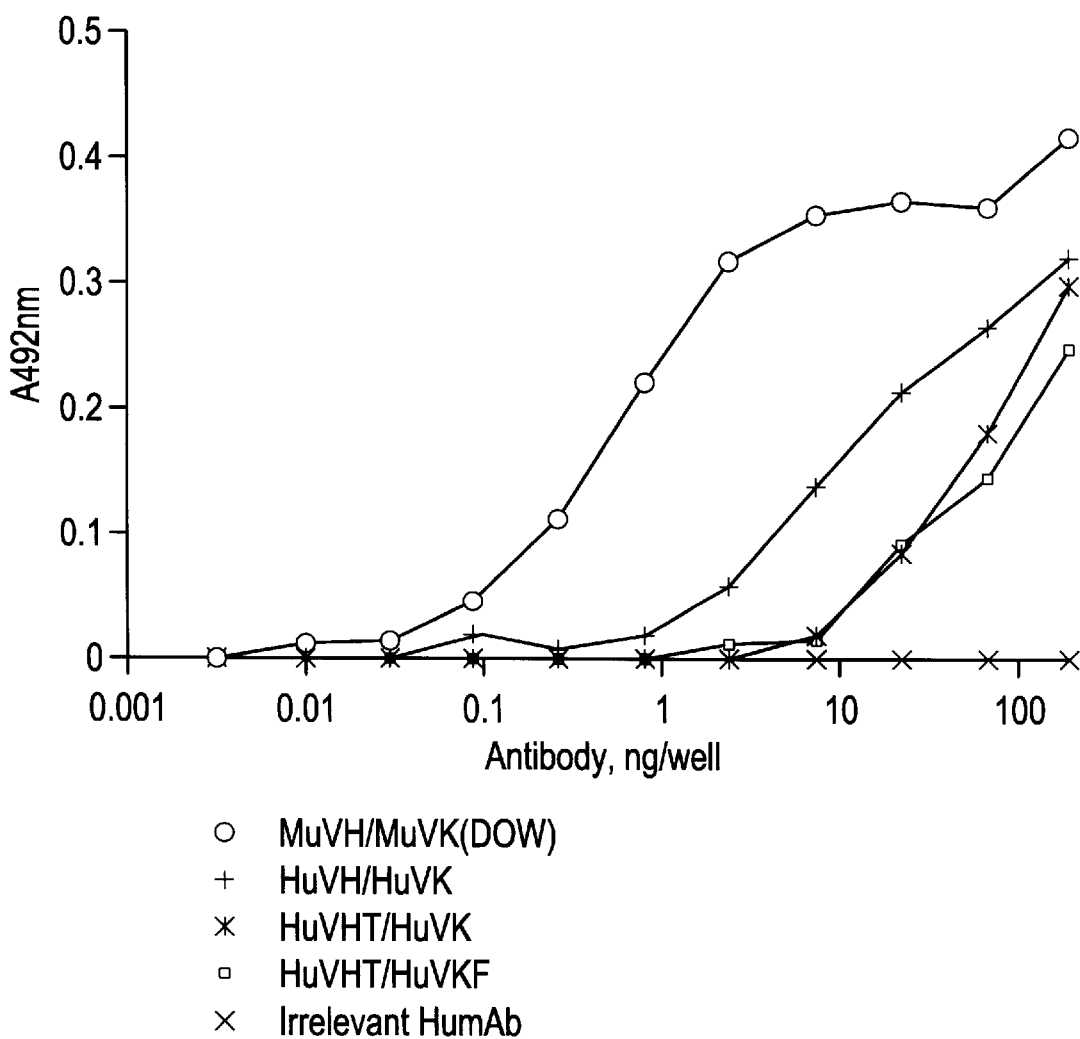

FIG. 6 contains results of ELISA assays with COL-1 antibodies including those produced according to the invention.

Figure 7:
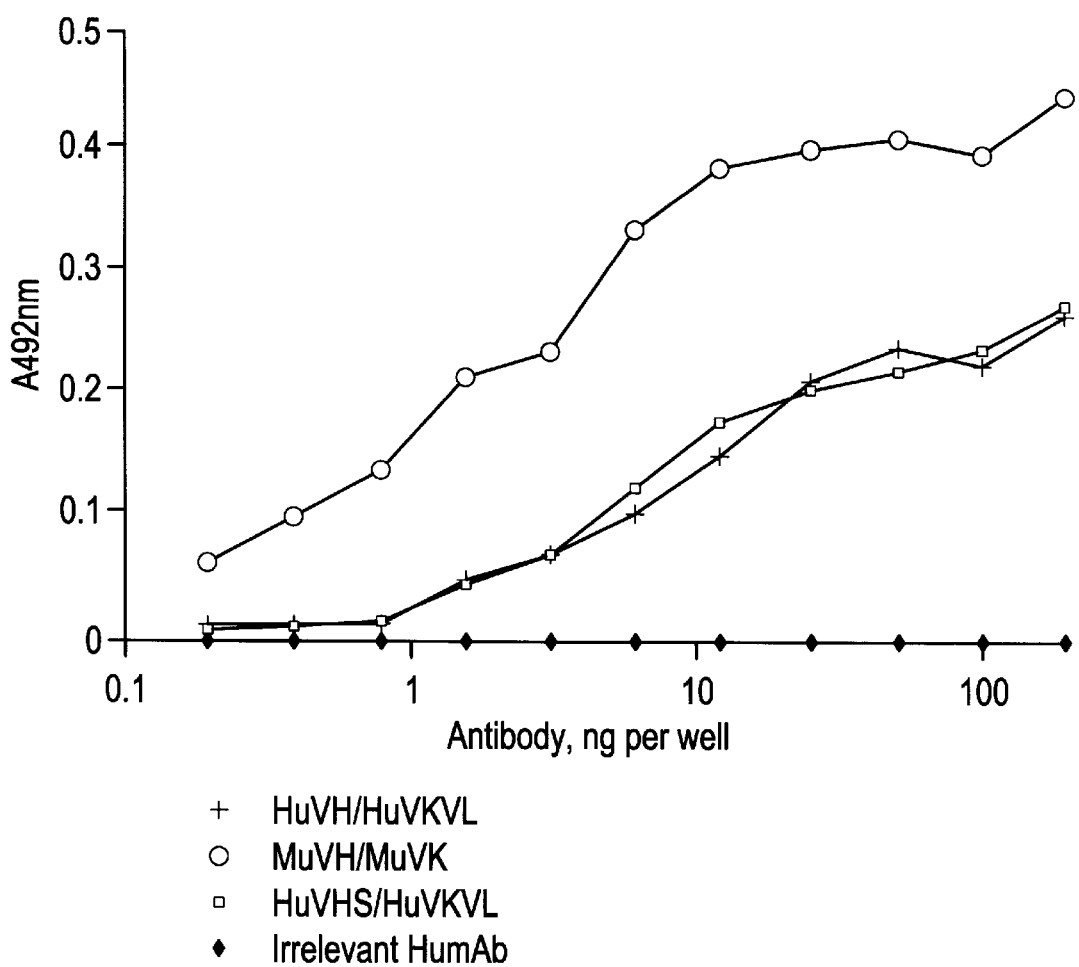

FIG. 7 contains results of ELISA assays with COL-1 antibodies including those produced according to the invention.

Figure 8:
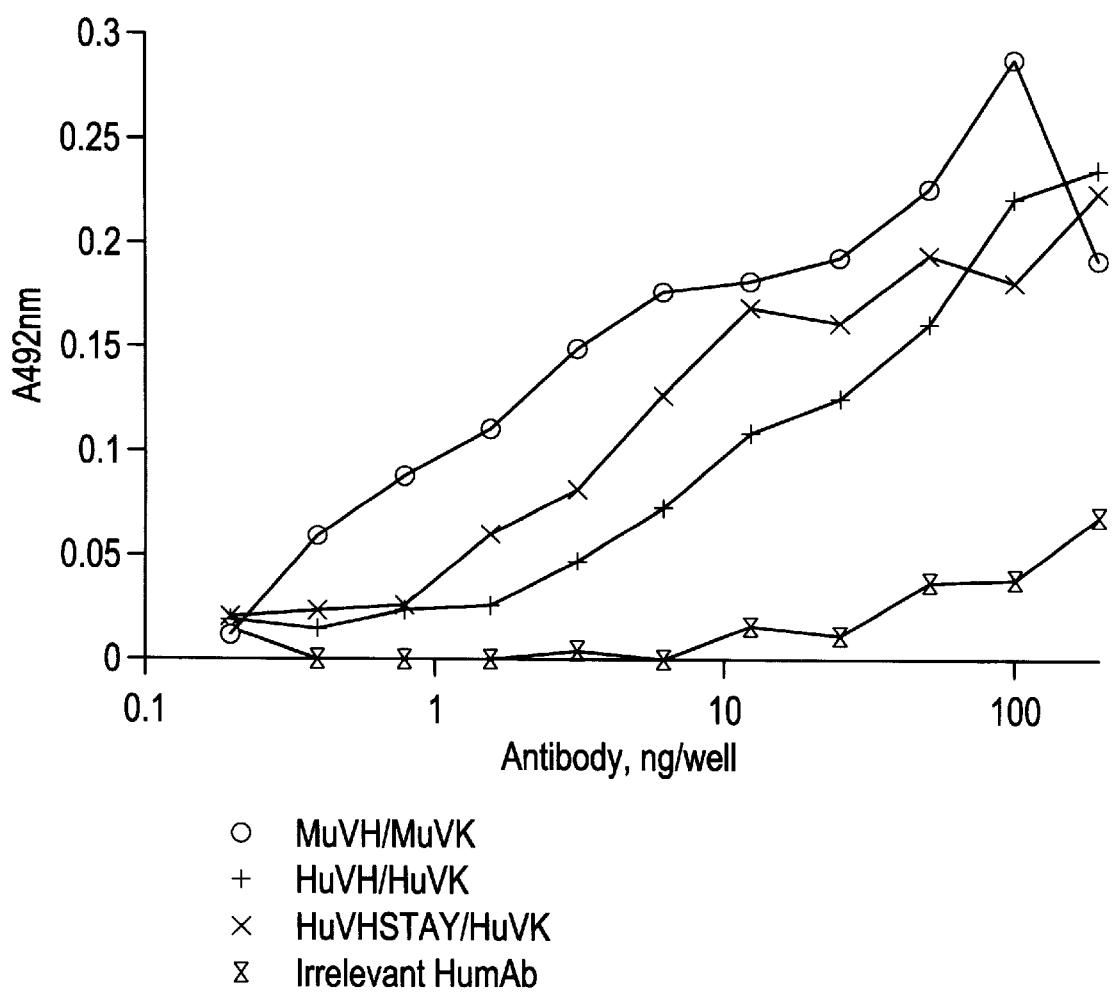

FIG. 8 contains results of ELISA assays with COL-1 antibodies including those produced according to the invention.

Figure 9:
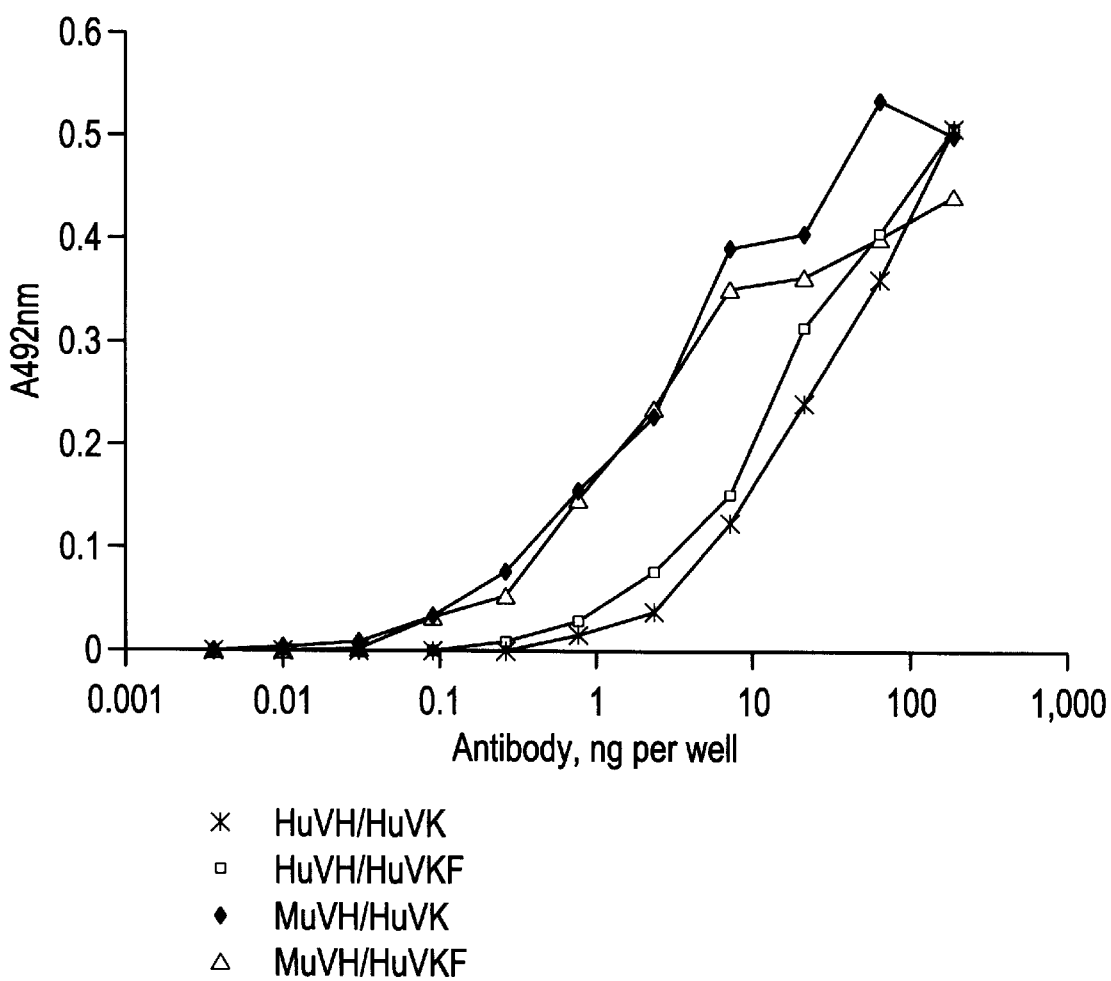

FIG. 9 contains results of ELISA assays with COL-1 antibodies including those produced according to the invention.

Figure 10:
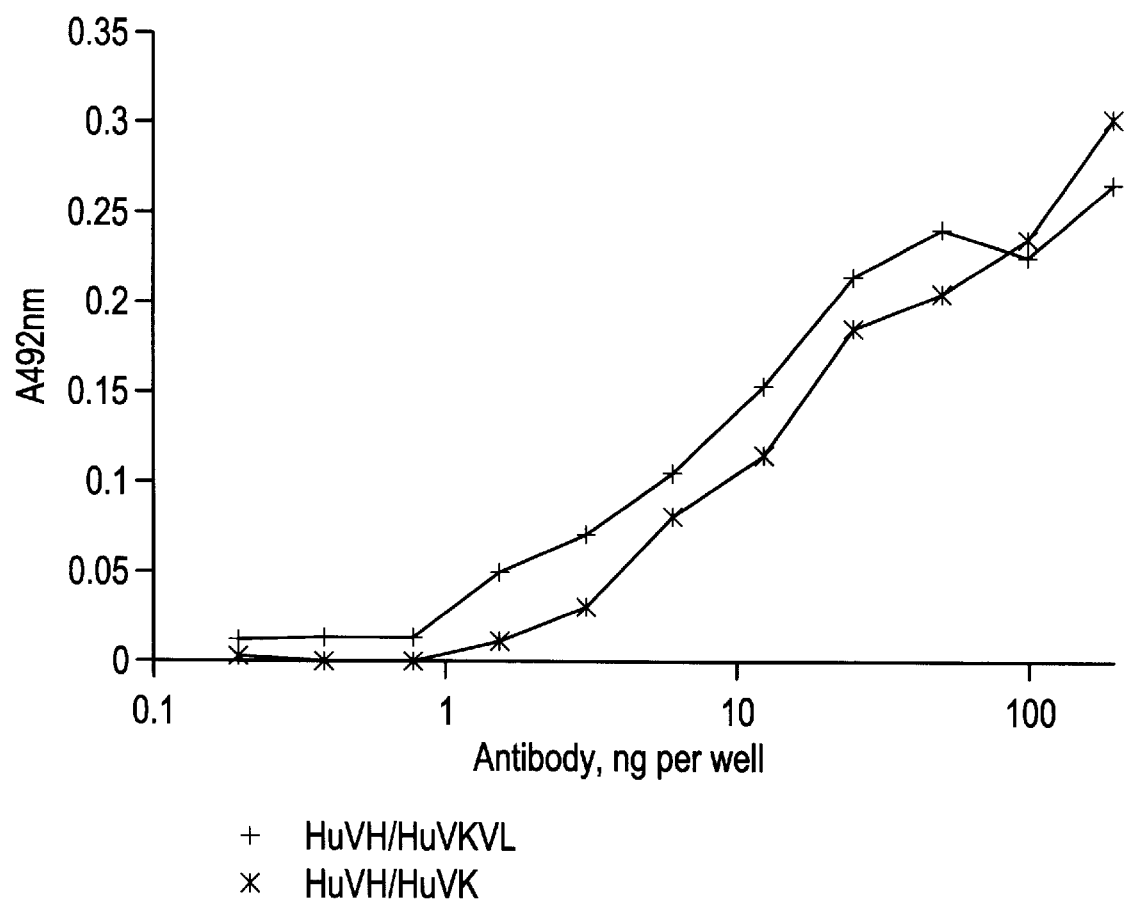

FIG. 10 contains results of ELISA assays with COL-1 antibodies including those produced according to the invention.

Figure 11:
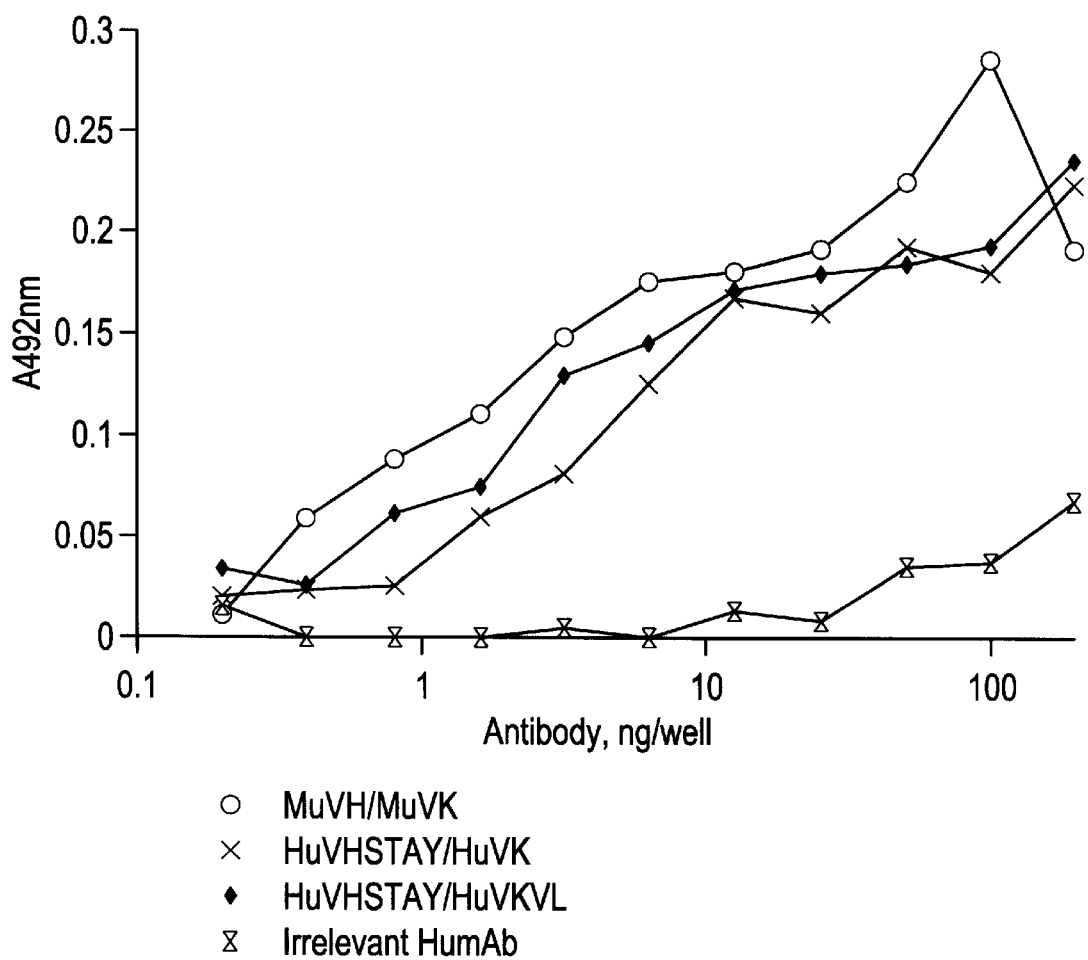

FIG. 11 contains results of ELISA assays with COL-1 antibodies including those produced according to the invention.

Figure 12:
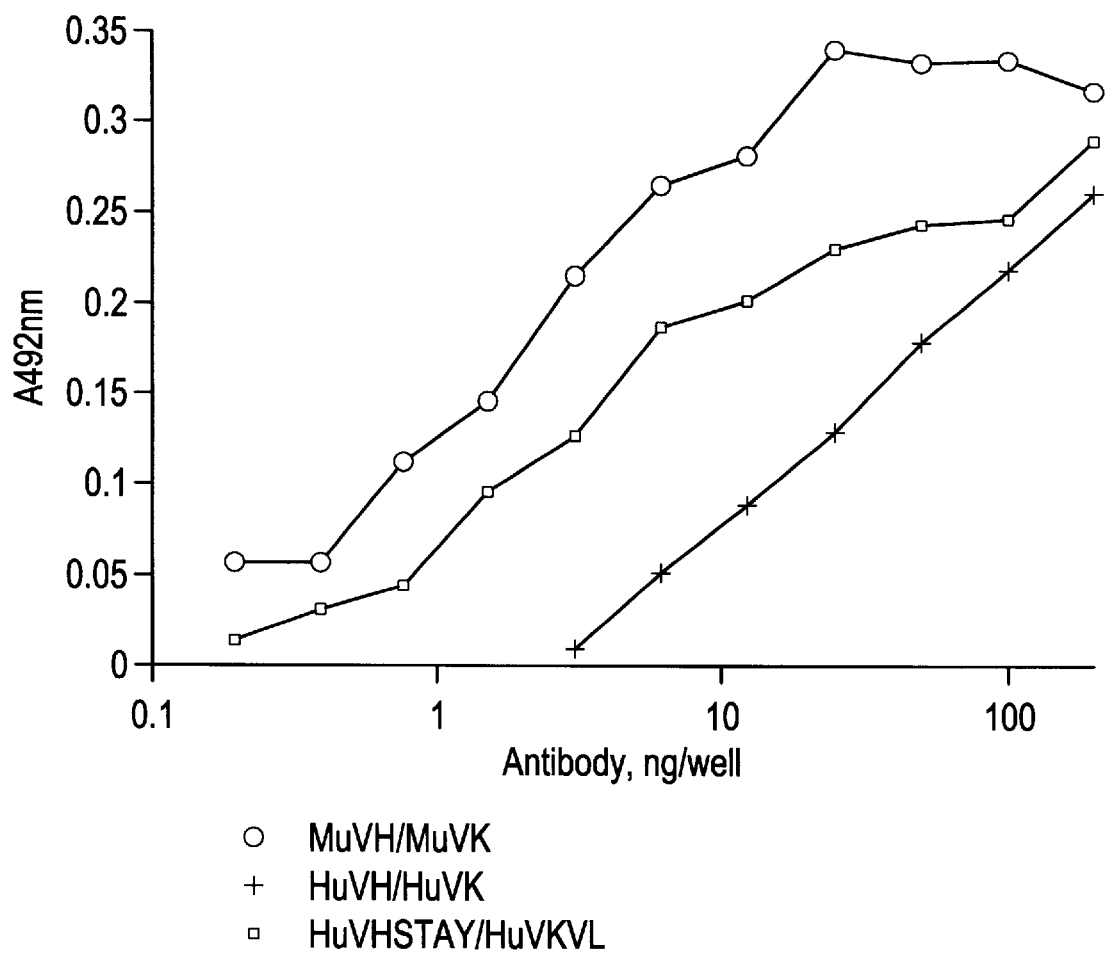

FIG. 12 contains results of ELISA assays with COL-1 antibodies including those produced according to the invention.

FIG. 13 contains the amino acid sequence (SEQ ID NO:12) of the humanized $V_H$ expressed by the deposited cell line ATCC CRL-12208.

FIG. 14 contains the amino acid sequence (SEQ ID NO:16) of the humanized $V_K$ expressed by the deposited cell line ATCC CRL-12208.

FIG. 15 presents the nucleotide sequence of the DNA template use to produce the initial humanized COL-1 heavy chain variable region, HuVH.

FIG. 16 presents the nucleotide sequence (SEQ ID NO:19) of the DNA template used to produce a variety of HuVH derivatives.

FIG. 17 presents the nucleotide sequence (SEQ ID NO:20) of the DNA template used to produce the initial humanized COL-1 light chain variable region, HuVK.

FIG. 18 presents the nucleotide sequence (SEQ ID NO:21) of the DNA template used to produce the HuVKVL derivative of HuVK.

DETAILED DESCRIPTION OF THE INVENTION

Prior to setting forth the invention, definitions of certain terms which are used in this disclosure are set forth below.

Antibody—This refers to single chain, two-chain, and multi-chain proteins and glycoproteins belonging to the classes of polyclonal, monoclonal, chimeric, and hetero immunoglobulins (monoclonal antibodies being preferred); it also includes synthetic and genetically engineered variants of these immunoglobulins. "Antibody fragment" includes Fab, Fab', F(ab')$_2$, and Fv fragments, as well as any portion of an antibody having specificity toward a desired target epitope or epitopes.

Humanized antibody—This will refer to an antibody derived from a non-human antibody, typically murine, that retains or substantially retains the antigen-binding properties of the parent antibody but which is less immunogenic in humans. This may be achieved by various methods including (a) grafting only the non-human CDRs onto human framework and constant regions with or without retention of critical framework residues, or (b) transplanting the entire non-human variable domains, but "cloaking" them with a human-like section by replacement of surface residues. Such methods as are useful in practicing the present invention include those disclosed in Jones et al., Morrison et al., *Proc. Natl. Acad. Sci. USA*, 81:6851–6855 (1984); Morrison and Oi, *Adv. Immunol.*, 44:65–92 (1988); Verhoeyen et al., *Science*, 239:1534–1536 (1988); Padlan, *Molec. Immun.*, 28:489–498 (1991); Padlan, *Molec. Immun.*, 31(3):169–217 (1994).

Complementarity Determining Region, or CDR—The term CDR, as used herein, refers to amino acid sequences which together define the binding affinity and specificity of the natural Fv region of a native immunoglobulin binding site as delineated by Kabat et al. (1991).

Framework Region—The term FR, as used herein, refers to amino acid sequences interposed between CDRs. These portions of the antibody serve to hold the CDRs in an appropriate orientation for antigen binding.

Constant Region—The portion of the antibody molecule which confers effector functions. In the present invention, murine constant regions are substituted with human constant regions. The constant regions of the subject chimeric or humanized antibodies are derived from human immunoglobulins. The heavy chain constant region can be selected from any of the five isotypes: alpha, delta, epsilon, gamma or mu. Further, heavy chains of various subclasses (such as the IgG subclasses of heavy chains) are responsible for different effector functions and thus, by choosing the desired heavy chain constant region chimeric antibodies with desired effector function can be produced. Preferred constant regions are gamma 1 (IgG1), gamma 3 (IgG3) and gamma 4 (IgG4). More preferred is a constant region of the gamma 1 (IgG1) isotype. The light chain constant region can be of the kappa or lambda type, preferably of the kappa type.

Chimeric antibody—This is an antibody containing sequences derived from two different antibodies, which typically are of different species. Most typically chimeric antibodies comprise human and murine antibody fragments, generally human constant and murine variable regions.

Mammals—Animals that nourish their young with milk secreted by mammary glands, preferably warm blooded mammals, more preferably humans.

Immunogenicity—A measure of the ability of a targeting protein or therapeutic moiety to elicit an immune response (humoral or cellular) when administered to a recipient. The present invention is concerned with the immunogenicity of the subject humanized antibodies or fragments thereof.

Humanized reduced immunogenicity—This refers to a humanized antibody exhibiting reduced immunogenicity relative to the parent antibody, typically a murine antibody such as COL-1.

Humanized antibody substantially retaining the binding properties of the parent antibody—This refers to a humanized antibody which retains the ability to specifically bind the antigen recognized by the parent antibody used to produce such humanized antibody. Preferably the humanized antibody will exhibit the same or substantially the same antigen-binding affinity and avidity as the parent antibody, e.g., COL-1. Ideally, the affinity of the antibody will not be less than 5% of the parent antibody affinity, more preferably not less than about 30%, and most preferably the affinity will not be less than 50% of the parent antibody. Methods for assaying antigen-binding affinity are well known in the art and include half-maximal binding assays, competition assays, and Scatchard analysis. Suitable antigen binding assays are described in this application.

In its broadest embodiment, the present invention is directed to humanized antibodies which specifically bind CEA, an antigen expressed by various human cancers, in particular gastrointestinal, colorectal, breast, lung, and ovarian cancers. Preferably, such humanized antibodies will be derived from antibodies having good binding affinity to CEA, such as COL-1 through COL-15 disclosed by Muraro et al., *Cancer Res.*, 45(11 Pt. 2):5769–5780 (1985).

Most preferably, such humanized antibodies will be derived from COL-1, a murine antibody of the IgG2a isotype, which has been reported to bind to CEA with high affinity ($1.4 \times 10^9$ M$^{-1}$) with no detectable cross-reactivity for CEA-related antigens, such as the non-specific cross-reacting antigen (NCA) and the normal fecal antigen (NFA).

As discussed above, humanized antibodies afford potential advantages over murine and also chimeric antibodies, e.g., reduced immunogenicity in humans. This is advantageous because it should reduce and potentially eliminate the eliciting of a HAMA response when such humanized antibodies are administered in vivo, e.g., either for treatment of cancer or for diagnosis of cancer as by tumor imaging. Also, such antibodies may exhibit improved plasma clearance, pharmacokinetic, and tumor targeting properties.

However, as noted above, humanization may in some instances adversely affect antigen binding. Preferably, the humanized αCEA antibodies of the present invention will possess a binding affinity for CEA of not less than about 5% and more preferably not less than about 30%, and most preferably not less than 50% of the CEA binding antigen affinity of the parent murine antibody, preferably COL-1. Most preferably, the humanized antibodies of the present invention will possess a binding affinity for CEA of not less than about 5% and more preferably not less than about 30% and most preferably not less than about 50% of the CEA binding affinity of COL-1, or a chimeric antibody derived therefrom.

Preferably, the humanized antibodies of the present invention will bind the same epitope as COL-1. Such antibodies can be identified based on their ability to compete with COL-1 for binding to CEA or to CEA-expressing cells.

In general, the subject humanized antibodies are produced by obtaining nucleic acid sequences encoding the variable heavy ($V_H$) and variable light chains ($V_L$, e.g., $V_K$) of an antibody which binds CEA (preferably COL-1), identifying the CDRs in said $V_H$ and $V_L$ sequences, and grafting such CDR-encoding nucleic acid sequences onto selected human framework-encoding nucleic acid sequences.

Preferably, the human framework amino acid sequences are selected such that the resulting antibody is likely to be suitable for in vivo administration in humans. This can be determined, e.g., based on previous usage of antibodies containing such human FRs. Preferably, the human FRs will not themselves be significantly immunogenic. Examples of such human frameworks include NEWM and REI.

Alternatively, the amino acid sequences of the FRs of the antibody to be humanized (e.g., COL-1) will be compared to those of known human FRs, and the human FRs to be used for CDR-grafting will be selected based on their comprising sequences highly similar to those of the parent antibody, e.g., a murine antibody which binds CEA. Numerous human FRs have been isolated and their sequences reported in the literature. This enhances the likelihood that the resultant CDR-grafted "humanized" antibody, which contains the CDRs of the parent (e.g., murine) antibody grafted onto the selected human FRs, will substantially retain the antigen binding structure and thus retain the binding affinity of the parent antibody. As a result of such studies, the FRs of REI and NEWM antibodies have been identified as having amino acid sequences which are likely to allow the CDRs of COL-1 To retain a significant degree of antigen binding affinity. As noted, the selected human framework regions will preferably be those that are expected to be suitable for in vivo administration, i.e., not immunogenic. Based on their amino acid sequences, REI and NEWM human framework regions are expected to be substantially non-immunogenic.

In either method, the DNA sequences encoding the $V_H$ and $V_L$ regions of the preferably murine αCEA antibody must be obtained. Methods for cloning nucleic acid sequences encoding immunoglobulins are well known in the art. Such methods will generally involve the amplification of the immunoglobulin-encoding sequences to be cloned using appropriate primers by polymerase chain reaction (PCR). Primers suitable for amplifying immunoglobulin nucleic acid sequences, and specifically murine variable heavy and variable light sequences, have been reported in the literature. After such immunoglobulin-encoding sequences have been cloned, they will be sequenced by methods well known in the art. This will be effected in order to identify the $V_{H^-}$ and $V_L$-encoding sequences, and more specifically the portions thereof which encode the CDRs and FRs. This can be effected by well known methods which include, e.g., those disclosed in U.S. Pat. No. 4,816,397 to Boss et al. and U.S. Pat. No. 5,225,539 to Winter et al.

Once the DNA sequences encoding the CDRs and FRs of the antibody which is to be humanized have been identified, the amino acid sequences encoding the CDRs are then identified (deduced based on the nucleic acid sequences and the genetic code and by comparison to previous antibody sequences) and the CDR-encoding nucleic acid sequences are grafted onto selected human FR-encoding sequences. This may be accomplished by use of appropriate primers and linkers. Methods for selecting suitable primers and linkers to provide for ligation of desired nucleic acid sequences is well within the purview of the ordinary artisan.

As discussed above, the selected human FRs used for humanization will preferably be those that are likely to be suitable for in vivo administration, i.e. they are not in themselves immunogenic in humans (e.g., because of allotypic differences); examples thereof are REI and NEWM human FRs. Alternatively, the human FRs will be selected such that they comprise amino acid sequences which are highly similar to those of the parent antibody's FR sequences. This may be effected by comparing the amino acid sequences of the murine FRs to those of previously reported human FRs (see, e.g., Kabat et al., id.).

After the CDR-encoding sequences are grafted onto the selected human FR-encoding sequences, the resultant DNA sequences encoding the "humanized" variable heavy and variable light sequences will then be expressed to produce a humanized Fv or humanized antibody which binds CEA. Typically, the humanized $V_H$ and $V_L$ sequences will be expressed as part of a whole αCEA antibody molecule, i.e. as a fusion protein with human constant domain sequences whose encoding DNA sequences have been obtained from a commercially available library or which have been obtained using, e.g., one of the above-described methods for obtaining DNA sequences. However, the $V_H$ and $V_L$ sequences can also be expressed in the absence of constant sequences to produce a humanized αCEA Fv. Nevertheless, fusion of human constant sequences is potentially desirable because the resultant humanized αCEA antibody may possess human effector functions such as CDC and ADCC activity.

Methods for synthesizing DNA encoding a protein of known sequence are well known in the art. Using such methods, DNA sequences which encode the subject humanized $V_L$ and $V_H$ sequences (with or without constant regions) are synthesized, and then expressed in a vector system suitable for expression of recombinant antibodies. This may be effected in any vector system which provides for the subject humanized $V_L$ and $V_H$ sequences to be expressed as a fusion protein with human constant domain sequences and to associate to produce functional (antigen binding) antibodies or antibody fragments. Useful methods are set forth, e.g., in U.S. Pat. No. 4,816,397 to Boss et al. and U.S. Pat. No. 5,225,539 to Winter et al.

Expression vectors and host cells suitable for expression of recombinant antibodies and humanized antibodies in particular, are well known in the art. The following references are representative of methods and vectors suitable for expression of recombinant immunoglobulins which may be utilized in carrying out the present invention: Weidle et al., *Gene*, 51: 21–29 (1987); Dorai et al., *J. Immunol.*, 13(12) :4232–4241 (1987); De Waele et al., *Eur. J. Biochem.*, 176:287–295 (1988); Colcher et al., *Cancer Res.*, 49:1738–1745 (1989); Wood et al., *J. Immunol.*, 145(a) :3011–3016 (1990); Bulens et al., *Eur. J. Biochem.*, 195:235–242 (1991); Beggington et al., *Biol. Technology*, 10:169 (1992); King et al., *Biochem. J.*, 281:317–323 (1992); Page et al., *Biol. Technology*, 9:64 (1991); King et al., *Biochem. J.*, 290:723–729 (1993); Chaudary et al., *Nature*, 339:394–397 (1989); Jones et al., *Nature*, 321:522–525 (1986); Morrison and Oi, *Adv. Immunol.*, 44:65–92 (1988); Benhar et al., *Proc. Natl. Acad. Sci. USA*, 91:12051–12055 (1994); Singer et al., *J. Immunol.*, 150:2844–2857 (1993); Cooto et al., *Hybridoma*, 13(3): 215–219 (1994); Queen et al., *Proc. Natl. Acad. Sci. USA*, 86:10029–10033 (1989); Caron et al., *Cancer Res.*, 32:6761–6767 (1992); Cotoma et al., *J. Immunol. Meth.*, 152:89–109 (1992). Moreover, vectors suitable for expression of recombinant antibodies are commercially available. The vector may, e.g., be a bare nucleic acid segment, a carrier-associated nucleic acid segment, a nucleoprotein, a plasmid, a virus, a viroid, or a transposable element.

Host cells known to be capable of expressing functional immunoglobulins include, e.g.: mammalian cells such as Chinese Hamster Ovary (CHO) cells; COS cells; myeloma cells, such as NSO and SP2/O cells; bacteria such as *Escherichia coli*; yeast cells such as *Saccharomyces cerevisiae*; and other host cells. Of these, CHO cells are used by many researchers given their ability to effectively express and secrete immunoglobulins. NSO cells are one of the preferred types of host cells useful in the present invention.

Essentially, recombinant expression of humanized antibodies is obtained by one of two general methods. In the first method, the host cells are transfected with a single vector which provides for the expression of both $V_H$ and $V_L$ variable sequences optionally fused to selected constant regions. In the second method, host cells are transfected with two vectors, each of which provides for expression of either the $V_H$ or $V_L$ sequence, each optionally fused to a selected constant region.

Human constant domain sequences are well known in the art, and have been reported in the literature. Preferred human constant light chain sequences ($C_L$) include the kappa and lambda constant light sequences. Preferred human constant heavy chain sequences include human gamma 1, human gamma 2, human gamma 3, human gamma 4, and mutated versions thereof which provide for altered effect or function, e.g., enhanced in vivo half-life, reduced Fc receptor binding, and the like.

After expression, the antigen binding affinity of the resultant humanized antibody will be assayed by known methods, e.g., Scatchard analysis. Ideally, the antigen-binding affinity of the humanized antibody will approximate that of the parent antibody, e.g., COL-1. As discussed above, ideally the affinity of the humanized antibody will not be less than 5% of the parent antibody, more preferably not less than 30%, and most preferably not less than 50% of that of the parent antibody, e.g., COL-1.

In some instances, humanized antibodies produced by grafting CDRs (from an antibody which binds CEA) onto selected human FRs may provide humanized antibodies having the desired affinity to CEA. However, it may be necessary or desirable to further modify specific residues of the selected human FR in order to enhance antigen binding. This may occur because it is believed that some framework residues are essential to or at least affect antigen binding. Preferably, those framework residues of the parent (e.g., murine) antibody which maintain or affect combining-site structures will be retained. These residues may be identified by X-ray crystallography of the parent antibody or Fab fragment, thereby identifying the three-dimensional structure of the antigen-binding site.

These residues may potentially be identified by X-ray crystallography of the parent Fab, thereby identifying the three-dimensional structure of the antigen-binding site. Also, framework residues which may be involved in antigen binding may be putatively selected based on previously reported humanized murine antibody sequences. Thus, it may be beneficial to retain these and other murine framework residues from the parent murine antibody to optimize CEA binding. However, because of inherent unpredictability associated with amino acid modification of proteins, and antibodies in particular, the effects of such changes, if any, on antigen binding are unpredictable. Nevertheless, such methodology will ideally confer a "human-like" character to the resultant humanized antibody thus rendering it less immunogenic while retaining the interior and contacting residues which affect antigen-binding.

The present invention further embraces variants and equivalents which are substantially homologous to the humanized antibodies and antibody fragments set forth herein. These may contain, e.g., conservative substitution mutations, i.e. the substitution of one or more amino acids by similar amino acids. For example, conservative substitution refers to the substitution of an amino acid with another within the same general class, e.g., one acidic amino acid with another acidic amino acid, one basic amino acid with another basic amino acid, or one neutral amino acid by another neutral amino acid. What is intended by a conservative amino acid substitution is well known in the art.

The phrase "substantially homologous" is used in regard to the similarity of a subject amino acid sequence (of an oligo- or poly-peptide or protein) to a related, reference amino acid sequence. This phrase is defined as at least about 75% "correspondence"—i.e. the state of identical amino acid residues being situated in parallel—between the subject and reference sequences when those sequences are in "alignment," i.e. when a minimal number of "null" bases have been inserted in the subject and/or reference sequences so as to maximize the number of existing bases in correspondence between the sequences. "Null" bases are not part of the subject and reference sequences; also, the minimal number of "null" bases inserted in the subject sequence may differ from the minimal number inserted in the reference sequence. In this definition, a reference sequence is considered "related" to a subject sequence where both amino acid sequences make up proteins or portions of proteins which are either αCEA antibodies or antibody fragments with αCEA binding affinity. Each of the proteins comprising these αCEA antibodies or antibody fragments may independently be antibodies or antibody fragments or bi- or multi-functional proteins, e.g., such as fusion proteins, bi- and multi-specific antibodies, single chain antibodies, and the like.

The present invention is further directed to nucleic acid sequences from which such humanized antibodies and antibody fragments may be expressed, as well as expression vectors from which these humanized antibodies and antibody fragments may be expressed in transfected host cells.

In a preferred embodiment, such humanized antibodies and corresponding nucleic acid sequences will be derived from COL-1. Most preferably, the humanized $V_H$ sequence and the humanized $V_L$ sequence will have the sequences substantially as depicted in FIG. 1 or 13 or in FIG. 2 or 14, respectively, and as discussed in the Examples set forth below. However, as discussed, the invention further contemplates other modifications of these humanized $V_H$ and $V_L$ sequences, e.g., sequences which further comprise one or more conservative amino acid substitutions or which retain one or more additional murine framework residues which affect or do not significantly reduce antigen binding.

The subject humanized antibodies—because they specifically bind CEA (an antigen expressed on many different cancer cell types, e.g., lung carcinomas, breast carcinomas, gastrointestinal carcinomas such as stomach cancers, colorectal carcinomas such as colon cancers, ovarian carcinomas, etc.) and further because they will not be significantly immunogenic in humans—should be suitable for use as: therapeutics for the treatment or prevention of cancers characterized by CEA expression; diagnostic agents, e.g., for diagnosis and evaluating the prognosis of cancers characterized by CEA expression (based on levels of CEA expression); tumor imaging agents; or radiolabeled antibodies in the RIGS system (Radioimmunoguided Surgery system of Neoprobe Corp., Dublin, Ohio). See Hinkle et al., Antibody, Immunoconjugates and Radiopharmaceuticals, 4(3):339–358 (1991).

One skilled in the art would be able (by routine experimentation) to determine what amount of antibody would be effective and non-toxic for the purpose of treating cancer. Generally, however, an effective dosage will be in the range of about 0.05 to 100 milligrams per kilogram body weight per day.

The humanized antibodies or humanized antibody fragments of the invention may be administered to a human or other animal in accordance with the aforementioned methods of treatment in an amount sufficient to produce a therapeutic or prophylactic effect. The antibodies of the subject invention can be administered to such human or other animal in a conventional dosage form prepared by combining the antibody of the invention with a conventional, pharmaceutically acceptable carrier, diluent, and/or excipient according to known techniques. It will be recognized by one of ordinary skill in the art that the form and character of the pharmaceutically acceptable carrier, diluent, and/or excipient is dictated by the amount of active ingredient with which it is to be combined, the route of administration, and other well-known variables.

Pharmaceutically acceptable formulations may include, e.g., a suitable solvent, preservatives such as benzyl alcohol if desired, and a buffer. Useful solvent may include, e.g., water, aqueous alcohols, glycols, and phsophonate and carbonate esters. Such aqueous solutions contain no more than 50% by volume of organic solvent. Suspension-type formulations may include a liquid suspending medium as a carrier, e.g., aqueous polyvinylpyrrolidone, inert oils such as vegetable oils or highly refined mineral oils, or aqueous cellulose ethers such as aqueous carboxymethylcellulose. A thickener such as gelatin or an alginate may also be present, one or more natural or synthetic surfactants or antifoam agents may be used, and one or more suspending agents such as sorbitol or another sugar may be employed therein. Such formations may contain one or more adjuvants.

The route of administration of the antibodies (or fragment thereof) of the present invention may be oral, parenteral, by inhalation, or topical. The term parenteral as used herein includes intravenous, intramuscular, subcutaneous, rectal, vaginal, or intraperitoneal administration. The subcutaneous, intravenous, and intramuscular forms of parenteral administration are generally preferred.

The daily parenteral and oral dosage regimens for prophylactically or therapeutically employing humanized antibodies of the present invention will generally be in the range of about 0.005 to 100, but preferably about 0.5 to 10, milligrams per kilogram body weight per day.

The antibodies of the present invention may also be administered by inhalation. By "inhalation" is meant intranasal and oral inhalation administration. Appropriate dosage forms for such administration, such as an aerosol formulation or a metered dose inhaler, may be prepared by conventional techniques. The preferred dosage amount of a compound of the invention to be employed is generally within the range of about 0.1 to about 100, more preferably about 10 to 100, milligrams per kg body weight.

The antibody of the invention may also be administered topically. By topical administration is meant non-systemic administration. This includes the administration of a humanized antibody (or humanized antibody fragment) formulation of the invention externally to the epidermis or to the buccal cavity, and instillation of such an antibody into the ear, eye, or nose, and wherever it does not significantly enter the bloodstream. By systemic administration is meant oral, intravenous, intraperitoneal, subcutaneous, and intramuscular administration. The amount of an antibody required for therapeutic, prophylactic, or diagnostic effect will, of course, vary with the antibody chosen, the nature and severity of the condition being treated and the animal undergoing treatment, and is ultimately at the discretion of the physician. A suitable topical dose of an antibody of the invention will generally be within the range of about 1 to 100 milligrams per kilogram body weight daily.

Formulations

While it is possible for an antibody or fragment thereof to be administered alone, it is preferable to present it as a pharmaceutical formulation. The active ingredient may comprise, for topical administration, from 0.001% to 10% w/w, e.g., from 1% to 2% by weight of the formulation, although it may comprise as much as 10% w/w but preferably not in excess of 5% w/w and more preferably from 0.1% to 1% w/w of the formulation.

The topical formulations of the present invention, comprise an active ingredient together with one or more acceptable carrier(s) therefor and optionally any other therapeutic ingredients(s). The carrier(s) must be "acceptable" in the sense of being compatible with the other ingredients of the formulation and not deleterious to the recipient thereof.

Formulations suitable for topical administration include liquid or semi-liquid preparations suitable for penetration through the skin to the site of where treatment is required, such as liniments, lotions, ointments, creams or pastes, and drops suitable for administration to the eye, ear, or nose.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified and sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surface active such as sorbitan esters or polyoxyethylene derivatives thereof. Suspending agents such as natural gums, cellulose derivatives or inorganic materials such as silicaceous silicas, and other ingredients such as lanolin, may also be included.

Kits according to the present invention include frozen or lyophilized humanized antibodies or humanized antibody fragments to be reconstituted, respectively, by thawing (optionally followed by further dilution) or by suspension in a (preferably buffered) liquid vehicle. The kits may also include buffer and/or excipient solutions (in liquid or frozen form)—or buffer and/or excipient powder preparations to be reconstituted with water—for the purpose of mixing with the humanized antibodies or humanized antibody fragments to produce a formulation suitable for administration. Thus, preferably the kits containing the humanized antibodies or humanized antibody fragments are frozen, lyophilized, prediluted, or pre-mixed at such a concentration that the addition of a predetermined amount of heat, of water, or of a solution provided in the kit will result in a formulation of sufficient concentration and pH as to be effective for in vivo or in vitro use in the treatment or diagnosis of cancer. Preferably, such a kit will also comprise instructions for reconstituting and using the humanized antibody or humanized antibody fragment composition to treat or detect cancer. The kit may also comprise two or more component parts for the reconstituted active composition. For example, a second component part—in addition to the humanized antibodies or humanized antibody fragments—may be bifunctional chelant, bifunctional chelate, or a therapeutic agent such as a radionuclide, which when mixed with the humanized antibodies or humanized antibody fragments forms a conjugated system therewith. The above-noted buffers, excipients, and other component parts can be sold separately or together with the kit.

It will be recognized by one of skill in the art that the optimal quantity and spacing of individual dosages of a humanized antibody or humanized antibody fragment of the invention will be determined by the nature and extent of the condition being treated, the form, route and site of administration, and the particular animal being treated, and that such optima can be determined by conventional techniques. It will also be appreciated by one of skill in the art that the optimal course of treatment, i e., the number of doses of an antibody or fragment thereof of the invention given per day for a defined number of days, can be ascertained by those skilled in the art using conventional course of treatment determination tests.

The subject humanized antibodies may also be administered in combination with other anti-cancer agents, e.g., other antibodies or drugs. Also, the subject humanized antibodies or fragments may be directly or indirectly attached to effector moieties having therapeutic activity. Suitable effector moieties include by way of example cytokines (IL-2, TNF, interferons, colony stimulating factors, IL-1, etc.), cytotoxins (Pseudomonas exotoxin, ricin, abrin, etc.), radionuclides, such as $^{90}Y$, $^{131}I$, $^{99m}Tc$, $^{111}In$, $^{125}I$, among others, drugs (methotrexate, daunorubicin, doxorubicin, etc.), immunomodulators, therapeutic enzymes (e.g., beta-galactosidase), anti-proliferative agents, etc. The attachment of antibodies to desired effectors is well known. See, e.g., U.S. Pat. No. 5,435,990 to Cheng et al. Moreover, bifunctional linkers for facilitating such attachment are well known and widely available. Also, chelators (chelants and chelates) providing for attachment of radionuclides are well known and available.

Alternatively, the subject humanized αCEA antibodies or fragments may be used as immunodiagnostic agents both in vivo and in vitro. A particularly preferred usage is for in vivo imaging of cancer cell lesions which express CEA. The subject antibodies are preferred because they should elicit no significant HAMA or allergic response. Thus, they may be used repeatedly to monitor the disease status of a patient.

As noted above, another preferred application of the subject humanized antibodies or fragments thereof is in the RIGS system (Radioimmunoguided Surgery system of Neoprobe Corp., Dublin, Ohio). This technique involves the intravenous administration of a radiolabeled monoclonal antibody or its fragment prior to surgery. After allowing for tumor uptake and blood clearance of radioactivity, the patient is taken to the operating room where surgical exploration is effected with the aid of a hand-held gamma activity probe, e.g., the NEOPROBE® 1000. This helps the surgeon identify the tumor metastases and lessen the complications of excision.

The RIGS system (Radioimmunoguided Surgery system of Neoprobe Corp., Dublin, Ohio) is advantageous because it allows for the detection of tumors not otherwise detectable by visual inspection and/or palpation. See, O'Dwyer et al., *Arch. Surg.*, 121:1391–1394 (1986). This technique is described in detail in Hinkle et al., *Antibody, Immunoconjugates and Radiopharmaceuticals*, 4:(3)339–358 (1991). This reference discloses the use of this technique with αCEA antibodies including the COL-1 monoclonal antibody. This technique is particularly useful for cancers of the colon, breast, pancreas, and ovaries. Thus, this technique should be applicable to the subject humanized antibodies which react with CEA expressed by colon, breast, and ovarian cancers. Also, Hinkle et al. (id.) cite numerous references describing this technique. The subject humanized antibodies or fragments thereof may be radiolabeled with radionuclides which are suitable for in vivo administration, e.g., iodine radionuclides such as $^{131}I$ and $^{125}I$. Moreover, $^{111}In$ and $^{99m}Tc$ are also suitable.

The subject humanized antibodies may be used alone or in combination with other antibodies. Also, the subject humanized antibodies may be prepared in the form of a diagnostically effective composition. Generally, this will entail the incorporation of diagnostically acceptable carriers and excipients, and labels which provide for detection. Suitable labels include diagnostic radionuclides, enzymes, etc. Methods for using antibodies for tumor imaging are well known in the art.

Without further elaboration, it is believed that one skilled in the art can, using the preceding description, utilize the present invention to its fullest extent. The invention will be further clarified by a consideration of the following examples, which are intended to be purely exemplary of the present invention and thus to be construed as merely illustrative examples and not limitations of the scope of the present invention an any way.

EXAMPLES

Materials and Methods
DNA Template Preparation

All recombination work was performed upon DNA sequences in plasmid M13 vectors. The source of the NEWM framework regions for producing the initial humanized COL-1 VH was an M13 construct bearing—between the M13 BamH I and Hind III sites—a DNA segment having the nucleotide sequence shown in FIG. 13. The source of REI framework regions for producing the initial humanized COL-1 VL was an M13 construct bearing—between the M13 BamH I and Hind III sites—a DNA segment encoding the REI amino acid sequence of FIG. 2.

When overlap-extension procedures were used to introduce mutations into a given DNA sequence, double stranded M13 DNA was utilized. In contrast, when extension-ligation procedures were used instead, the oligonucleotides were designed to anneal to only one of the two DNA strands. In this latter procedure, the M13 DNA was first treated to substitute uridine for every thymidine base in the DNA, to produce uridinylated DNA. This was accomplished by transfecting the M13 plasmid DNA into competent cells lacking dUTPase and uracil glycosylase, normally RZ1032 cells (though CJ236 cells available from Bio-Rad of Hercules, Calif., are also suitable) by combining the following ingredients.

1 μL of M13 plasmid DNA 4 mL of LB broth

40 μL of competent RZ1032 cells.

The culture was shaken for 5 hours at 37° C. and the resulting single-stranded plasmid DNA (ssDNA) was isolated and dissolved in 50 μL Tris-EDTA buffer. The DNA was then treated with uracil glycosylase by mixing together:

1 μL uridinylated ssDNA

1 μL 10×glycosylase buffer

1 U uracil glycosylase (Gibco BRL, Gathersburg, Md.)

40 μL 25 mM $MgCl_2$.

This mixture was then incubated at 37° C. for one hour and then 6.6 μL 25 mM $MgCl_2$ and 9.9 μL 1M NaOH. The mixture was then further incubated for 5 minutes at 37° C. and 16.5 μL of 0.6M HCl was then added to neutralize the mixture. The DNA was then ethanol precipitated and dissolved in water.

M13 Oligonucleotide Primers

The following oligonucleotide primers were used throughout the process of preparing the humanized COL-1 VHs and VLs exemplified below.

10. 5'-CTAAAACGACGGCCAGT-3' (SEQ ID NO:22) and 11. 5'-AACAGCTATGACCATG-3' (SEQ ID NO:23) (both for using in producing VHs); and 385. 5'-GCGGGCCTCTTCGCTATTACGC-3' (SEQ ID NO:24) and 391. 5'-CTCTCTCAGGGCCAGGCGGTGA-3' (SEQ ID NO:25) (both for use in producing VKs).

These primers are complementary to regions of the plasmid M13 which are external both to the (NEWM or REI) target framework sequences and to the BamH I site -to- Hind III site section of Ml13.

Murine Variable Regions

In order to compare the antibody binding characteristics of the antibodies produced according to the examples set forth below, antibodies having a chimeric heavy chain (i.e. a heavy chain having a murine COL-1 VH region and a human IgG1 constant region) and/or a chimeric light chain (i.e. a light chain having a murine COL-1 VL and a human κ constant region) were expressed. The source of these chimeric chains was the ATCC-deposited cell line CRL 11217 (Budapest) which expresses a chimeric COL-1 antibody having both chains. The heavy chain of this antibody was termed "MuVH" and the light chain thereof was termed "MuVL."

Oligonucleotide Phosphorylation Protocol

Mutating oligonucleotides used in non-overlap extensions were phosphorylated according to the procedure below. In a final volume of 25 μL, the following ingredients were combined:

10 pmol of each oligonucleotide,

5 μL of a 5×polynucleotide kinase buffer, and

5 U of T4 polynucleotide kinase (Gibco BRL).

The phosphorylation reaction was started with the addition of the enzyme and allowed to proceed for one hour at 37° C.

Annealing Protocol for Non-Overlap Extension-Ligations

The annealing step for non-overlap extension-ligations involved performing one annealing in which all mutation-carrying oligonucleotides and one primer oligonucleotide were annealed to a single stranded DNA template in which all thymidine bases had been replaced with uridine bases. The mutating oligonucleotides were first phosphorylated according to the above oligonucleotide phosphorylation protocol. In a final volume of 20 μL, the following ingredients were combined:

1 pmol of each mutation-carrying phosphorylated oligonucleotide 1 pmol of a primer oligonucleotide 4 μL 5×annealing buffer 0.2 pmol ssU-DNA template The mixture was then heated to 90° C. for 30 sec., then quickly cooled to 70° C., and finally allowed to slowly cool to 37° C.

Extension-Ligation Protocol for Non-Overlap Extension-Ligations

After completion of the annealing step in which the primer and phosphorylated mutating oligonucleotides were annealed to the ssU-DNA template, extension-ligation was performed as follows. In a final volume of 30 μL, the following ingredients were combined:

20 μL annealed ssU-DNA (i.e. the contents of the above annealing procedure)

2 μL 5×annealing buffer

2 μL 0.1M dithiothreitol 0.3 μL 0.1M ATP

1 μL 6.25 mM dNTP mixture of equimolar amounts of dATP, dTTP, dGTP, dCTP 2.5 U T7 DNA polymerase (USB, now Amersham Life Sciences, Cleveland, Ohio)

0.5 U T4 DNA ligase (Gibco BRL)

Water to 30 μL

This mixture was then incubated at room temperature for 1 hour.

Standard PCR Protocols

The following procedure was used, alternately, both to amplify the non-overlap extension-ligation DNA sequences and to perform extension of each overlap DNA sequence. In a final volume of 50 μL, the following ingredients were combined:

2 μL template DNA (either annealed ssU-DNA or non-annealed ssDNA)

5 μL 10×Vent buffer (NEB, i.e. New England Biolabs, Beverly, Mass.) or 10×Thermalase buffer (IBI of New Haven, Conn.)

2 μL 6.25 mM dNTP mixture of equimolar amounts of dATP, dTTP, dGTP, dCTP 25 pmol of one oligonucleotide primer 25 pmol of either a mutation-carrying oligonucleotide (for overlap-extension) or a second oligonucleotide primer 1 U Vent DNA polymerase (NEB) or Thermalase DNA polymerase (IBI)

Reactions were initiated with the addition of the DNA polymerase and then treated with about 15 cycles of: (1) 94° C. for 30 sec., (2) 50° C. for 30 sec., and (3) 30–60 seconds at either 75° C. (for Vent DNA polymerase) or 72° C. (for Thermalase). Reactions were brought to completion with 5 minutes at a constant temperature of either 75° C. (for Vent DNA polymerase) or 72° C. (for Thermalase).

PCR Overlap-Extension Amplification Protocol

After a pair of PCR reactions were performed—one for each of the two (partially complementary) overlapping DNA segments, the two resulting segments were joined according to the following PCR procedure. In a final volume of 50 μL, the following ingredients were mixed: a human κ light chain constant domain; the pSVhyg vector used in the "aLys-17" shown in FIG. 5. Each humanized variable region construct was inserted adjacent to the respective constant region, i.e. so as to replace either the HuVHLYS or the HuVLLys segment illustrated in FIG. 5.

The resulting vectors were transfected into NSO cells as follows. About 3 μg of the VH vector, or about 6 μg of the VL vector, produced by the pSV-insertion procedures, was then lineariized by digestion with 10 U PvuI (Gibco BRL). The digested DNA was then precipitated with ethanol and redissolved in 50 μL of water. NSO cells were collected by centrifugation and resuspended in 0.5 mL Dulbecco's Modified Eagle's Medium (DMEM) and then transferred to a Gene Pulser cuvette (Bio-Rad). The DNA from both one VH and one VL construct was gently mixed with the cells by pipetting and the cuvette was left on ice for 5 minutes. Next, the cuvette was inserted between the electrodes of the Bio-Rad Gene Pulser and a single pulse of 170V at 960 μF was applied. The contents of the cuvette were then transferred to a flask containing 20 mL DMEM and the cells were allowed to rest for 1–2 days at 37° C. Cells were again harvested by centrifugation and resuspended in 36 mL selective DMEM. 1.5 mL aliquots of this resuspension were placed in each well of a 24-well plate and incubated at 37° C. for 4 days, at which time the medium in each well was replaced with 1.5 mL of fresh selective DMEM. After 6 more days of incubation at 37° C., surviving cell colonies were visible to the naked eye and the supernatants of each well were assayed for antibody production. Both whole antibody production (i.e. without purification) and purified antibody production were assayed. To obtain purified antibodies, the supernatants were passed through a protein A column.

ELISA Assay Protocols

Antibody concentrations and antibody binding characteristics were tested using enzyme-linked immunosorbent assay (ELISA) procedures which are set forth as follows 1 αL of each overlap DNA (from the above overlap PCR extension reactions)

5 μL 10×Vent buffer (NEB) or Thermalase buffer (IBI)

2 μL 6.25 mM dNTP mixture of equimolar amounts of dATP, dTTP, dGTP, dCTP 25 pmol of each oligonucleotide primer used in the overlap PCR extensions 1 U Vent DNA polymerase (NEB) or Thermalase DNA polymerase (IBI)

Reactions were initiated with the addition of the DNA polymerase and then treated with about 15 cycles of: (1) 94° C. for 30 sec., (2) 50° C. for 30 sec., and (3) 30–60 seconds at either 75° C. (for Vent DNA polymerase) or 72° C. (for Thermalase). Reactions were brought to completion with 5 minutes at a constant temperature of either 75° C. (for Vent DNA polymerase) or 72° C. (for Thermalase).

Transfer of Humanized COL-1 Variable Region DNA Sequences from M13 to pSV Vectors and Subsequent Antibody Expression Humanized antibodies were expressed in pSV vectors grown in NSO cells as follows. The humanized variable region constructs which were produced in the plasmid, M13, were obtained by ethanol precipitating the M13 plasmids (as cytosolic DNA), redissolving them in aqueous solution, and digesting them with 10 U each of Hind III and BamH I (both from BRL, i.e. Gibco BRL) for 1 hour at 37° C. in a final volume of 100 μL with Tris-EDTA buffer. The resulting DNA fragments were then run on a low melting point agarose gel, the band containing the humanized construct DNA was cut out, and the DNA was purified using an ELUTIP 'd' column with 20 μL Tris-EDTA buffer. 10 μL of the purified DNA preparation was then combined with 1 μL of a Hind III and BamH I-digested pSV preparation, 3 μL of 5×ligase buffer, and 1 U of T4 DNA ligase (BRL), in order to insert the construct into a pSV plasmid. Humanized COL-1 VH constructs were inserted into pSVgpt vectors bearing a human IgG1 heavy chain constant region; the pSVgpt vector used is the "aLYS-30" shown in FIG. 5. Humanized COL-1 VL constructs were inserted into pSVhyg vectors bearing Measurement of IG Concentration The concentration of IgG secreted from transfected cells was measured using an enzyme-linked immunosorbent assay (ELISA) procedure which is set forth as follows.

Polyvinyl chloride (PVC) microtiter plates (Dynatech Laboratories, Chantilly, Va., catalog # 001-010-2101) were coated with goat anti-human IgG (10 mg/mL, GAHIG, Southern Biotechnology Associates, Inc., Birmingham, Ala., catalog # 2010-01) diluted with Milli-Q® water and placed on the plates using 50 mL/well. Plates were air-dried overnight at ambient temperature or at 37° C. for 3 hours. Prior to use, non-specific binding was blocked the addition of 0.2 mL/well of 1% (w/v) bovine serum albumin (Sigma, St. Louis, Mo. catalog # A7888) in phosphate buffered saline (Sigma, catalog # 1000-3) (PBS/BSA). All incubations were carried out in a humidified container. Plates were incubated for 1–2 hours at 37° C. and the blocking solution removed prior to sample addition. Two-fold serial dilutions of samples or a standard IgG solution set at 500 ng/mL (50 ml/well) were made in triplicate in the PBS/BSA solution. The plate was incubated at 37° C. for 3 hours or overnight at 4° C. The plate was washed 3-times with 0.025% Tween-20 (v/v, Sigma) using an automatic plate washer. 50 ml/well of 1:1000 dilution of a goat anti-human IgG conjugated to Horseradish Peroxidase (Southern Biotechnology Associates Inc.) was added and incubated at 37° C. for 1.5 hours. The wells were washed 3 times with 0.025% Tween-20 (v/v, Sigma) using an automatic plate washer and 50 ml/well OPD substrate buffer added. The color was developed for 4 minutes, stopped with 12.5 ml 12.5% $H_2SO_4$ and the absorbance at 492 nm read. The concentration of IgG in the test sample was estimated by comparison of the mean of the optical densities a standard curve constructed from the standard IgG.

Determination of Relative Affinities of Humanized Antibodies

Antibody binding characteristics were tested in an ELISA using partially purified CEA antigen immoblizied on Polyvinyl chloride (PVC) microtiter plates (Dynatech Laboratories, Chantilly, Va., catalog # 001-010-2101).

PVC plates were coated with 50 ml/well CEA (Dow Chemical, lot #040191), diluted 1:300 in Milli-Q water. Plates were air-dried overnight at ambient temperature or at 37° C. for 3 hours. Prior to use, non-specific binding was blocked by the addition of 0.2 mL/well of 1% (w/v) bovine serum albumin (Sigma, St. Louis, Mo. catalog # A7888) in phosphate buffered saline (Sigma, catalog # 1000-3) (PBS/BSA). Plates were incubated for 1–2 hours at 37° C. and the blocking solution removed prior to sample addition. All incubations were carried out in a humidified container. Two-fold serial dilutions (starting concentration range of 1.0 μg/ml–10 mg/ml) of the samples to be tested in the PBS/BSA solution were added to triplicate wells of the TAG-coated plate (50 ml/well). The plate was incubated overnight at 4° C. or 1–2 hours at 37° C. The plate was washed 3-times with 0.025% Tween-20 (v/v, Sigma) using an automatic plate washer. 50 ml/well of 1:1000 dilution of a goat anti-human IgG conjugated to Horseradish Peroxidase (Southern Biotechnology Associates Inc.) was added and incubated at 37° C. for 1.5 hours. The wells were washed 3 times with 0.025% Tween-20 (v/v, Sigma) using an automatic plate washer and 50 ml/well OPD substrate buffer added. The color was developed for 4 minutes, stopped with 12.5 ml 12.5% $H_2SO_4$ and the absorbance at 492 nm read.

Determination of Affinity Constants for Binding to CEA

Two-fold dilutions of purified Hu-COL-1 were prepared in PBS/BSA over a range of 1.0 μg/ml–0.003 mg/ml and samples (20 ml/well) were applied in triplicate to TAG-coated PVC prepared and blocked as described supra. Plates were incubated overnight at 4° C. Following this incubation, samples were transferred from the plate to the corresponding wells on the GAHIG-coated trap plate. The original TAG plate was washed 3-times with 0.025% Tween-20 (v/v, Sigma, catalog # P1379) using an automatic plate washer. An $^{125}$I-labeled goat anti-human IgG probe (ICN Biomedicals, Inc., catalog # 68088) was diluted to 75,000 cpm/25 ml in PBS/BSA and added (25 ml/well) to all wells. This TAG plate was incubated for 1 hour at 37° C.

After a 1 hour incubation at 37° C., the trap plate was washed as described above and $^{125}$I-labeled GAHIG probe was added. This plate was incubated for 1 hour at 37° C. Both plates (TAG and GAHIG-trap) containing probe were then washed with a microplate washer to remove the unbound probe. A plate cutter (D. Lee, Sunnyvale, Calif., Model HWC-4) was used to separate the wells from the plate frame. The radioactivity in each well was quantified by a gamma counter. The resulting data was analyzed according to the method of Scatchard (*Ann. NY Acad.*, 51:600–672 (1946)).

EXAMPLE 1

Synthesis of Initial CDR-Grafted (Humanized) Antibody from Murine COL-1

We describe in this Example the construction of humanized COL-1 Mabs (COL-1 HuVH/HuVK) using the $V_L$ and $V_H$ frameworks of human Mabs REI and NEWM, respectively. The CDRs for murine COL-1 were grafted onto human frameworks according to known methods as discussed supra. In particular, human frameworks were selected from antibodies which, based on previous studies, were predicted to be suitable, i.e. which should not adversely affect antigen binding and not exhibit significant immunogenicity in humans. The human frameworks selected for the variable heavy and variable light chains, respectively, were NEWM and REI.

In the production of the initial version of the humanized VH, certain murine framework residues were also retained which, based on previous studies, might allow retention of antigen binding properties. Specifically, residues F27, N28, I29, K30, N97, and T98 of the murine heavy chain were initially retained.

The production of this NEWM-grafted humanized COL-1 $V_H$ was accomplished using two rounds of a dual PCR procedure: the standard PCR protocol (for overlap-extension) followed by PCR amplification with oligonucleotide primers 10 and 11. This procedure was carried out as described above using a single-stranded M13 DNA template bearing, between the Hind III and BamH I sites thereof, a DNA segment having the nucleotide sequence shown in FIG. 15. The mutating oligonucleotides used in the first round (with Vent DNA polymerase) were designed and synthesized with the following sequences:

836. 5'-TGAGAATGGTGATACTGAATATGCCCCG-AAGT; (SEQ ID NO:26) and 837. 5'-TCGGGGCATATTCAGTATCACCATTCTC-AGGATC-3' (SEQ ID NO:27).

Those for the second round (with Thermalase) were:

838. 5'-ACTATGATTACGACGCGTTGGTTCTTCG-ATGTCTGGGGCCAAGGGTCCTTGGTCACCGT-C-3' (SEQ ID NO:28); and 839. 5'-ACGCGTCGTAATCATAGTAGATAGACC-CCGTGTATTACAGTAATAGACCGCGGTG-3' (SEQ ID NO:29).

The resulting humanized VH was named COL1NMVH or "HuVH."

In the production of the initial version of the humanized VL, no uniquely murine framework residues were retained. The production of the REI-grafted humanized COL-1 VL was accomplished by using two rounds of a procedure involving performing the annealing and extension-ligation protocols described above—followed by amplification by the standard Thermalase PCR protocol—using a ssM13 template bearing, between the Hind III and BamH I sites thereof, a ssU-DNA segment produced by the above procedure using the REIVK sequence shown in FIG. 17 (or in the second round, the mutated M13 template resulting from the first round). The mutating oligonucleotides used in round number 1 were designed and synthesized with the following sequences:

842. 5'-TATAGCCAGATGCACTGACACTTTTGCT-GGCCCTACAGGTGATG-3' (SEQ ID NO:30);

844. 5'-GCTCTGGGTCATCTGGATGTCGG-3' (SEQ ID NO:31);

849. 5'-TTCTACTCACGTGTGATTTGCAGCTTG-GTCCCTTGGCCGAACGTAGGAAGCTCCCTAC-TGTGCTGGCAGTAG-3' (SEQ ID NO:32);

850. 5'-ATGGTGAAGGTGTAGTCGGTACCGC-3' (SEQ ID NO:33); and 851. 5'-GCCTTACCTGGCGTCTGCTGGTACC-3' (SEQ ID NO:34).

The mutating oligonucleotide used in the second round was:

841. 5'-GCACACCAGATTGTAGGTTGGATGCAAGG-3' (SEQ ID NO:35).

The resulting humanized VL was called "COL1REVK" or "HuVK."

Concurrently, a second humanized COL-1 VL was made by the same procedure using the following mutating oligonucleotides.

For round 1:
842. 5'-TATAGCCAGATGCACTGACACTTTTGCTGGCCCTACAGGTGATG-3' (SEQ ID NO:30);
844. 5'-GCTCTGGGTCATCTGGATGTCGG-3' (SEQ ID NO:31);
849. 5'-TTCTACTCACGTGTGATTTGCAGCTTGGTCCCTTGGCCGAACGTAGGAAGCTCCCTACTGTGCTGGCAGTAG-3' (SEQ ID NO:32); and
851. 5'-GCCTTACCTGGCGTCTGCTGGTACC-3' (SEQ ID NO:34).

For round 2:
841. 5'-GCACACCAGATTGTAGGTTGGATGCAAGG-3' (SEQ ID NO:35).

The resulting VL was termed "HuVKF."

A number of amino acid substituted-versions of HuVH and HuVK were also constructed, using the above-described overlap extension technique employing oligonucleotide primers 10 and 11 or primers 385 and 391, followed by PCR amplification with Vent DNA polymerase. The mutating oligonucleotides and DNA templates are described below under their resulting humanized variable region name:

HuVHT (using the HuVH DNA shown in FIG. 16 as a template)
954. 5'-GACAATGCTGACAGACACCAGCAA-3' (SEQ ID NO:36) and
955. 5'-TGCTGGTGTCTGTCAGCATTGTCA-3' (SEQ ID NO:37);

HuVHS (using the HuVH DNA as a template)
684. 5'-CACCAGCAGCAACCAGTTCAG-3' (SEQ ID NO:38) and
683. 5'-ACTGGTTGCTCGTGGTGTCTA-3' (SEQ ID NO:39), HuVHSTAY (using the HuVHS DNA as a template)
1026. 5'-ACCAGCAGCAACACAGCCTACCTGAGACTCAGCAG-3' (SEQ ID NO:40) and
1028. 5'-TGCTGAGTCTCAGGTAGGCTGTGTTGCTGCTGGTGT-3' (SEQ ID NO:41);

HuVHA (using the HuVH DNA as a template)
745. 5'-TGACCTGCACCGCGTCTGGCTTCAAC-3' (SEQ ID NO:42) and
746. 5'-TTGAAGCCAGACGCGGTGCAGGTCAG-3' (SEQ ID NO:43);

HuVHAA (using the HuVHA DNA as a template)
1071. 5'-GAGACTCAGCAGCGTGACAG-3' (SEQ ID NO:44) and
1072. 5'-CGCTGCTGAGTCTCAGGCTGAATGTGTTCTTGCTGGTGTC-3' (SEQ ID NO:45);

HuVHAT (using the HuVHA DNA as a template)
1071. 5'-CCTGAGACTCAGCAGCGTGACAG-3' (SEQ ID NO:44) and
1074. 5'-CGCTGCTGAGTCTCAGGCTGGCCTGGTTCTTGCTGGTG-3' (SEQ ID NO:45);

HuVHAY (using the HuVHA DNA as a template)
1071. 5'-CCTGAGACTCAGCAGCGTGACAG-3' and
1073. 5'-CGCTGCTGAGTCTCAGGTAGAACTGGTTCTTGC-3' (SEQ ID NO:47);

HuVHATAY (using the HuVHA DNA as a template)
1071. 5'-CCTGAGACTCAGCAGCGTGACAG-3' (SEQ ID NO:44) and
1075. 5'-CGCTGCTGAGTCTCAGGTAGGCTGTGTTCTTGCTGGTGTC-3' (SEQ ID NO:48);

HuVHASTAY (using the HuVHS DNA as a template)
745. 5'-TGACCTGCACCGCGTCTGGCTTCAAC-3' (SEQ ID NO:42) and
746. 5'-TTGAAGCCAGACGCGGTGCAGGTCAG-3' (SEQ ID NO:43); and HuVKVL (using the HuVK DNA shown in FIG. 18 as a template)
1010. 5'-ACTCCGACATCGTGCTGACCCAGAG-3' and
1011. 5'-CTCTGGGTCAGCACGATGTCGGAG-3' (SEQ ID NO:49).

The above-produced M13 DNA constructs were transferred to pSV vectors which were then transfected into NSO host cells, according to the above-described procedures. The VH construct- and VL construct-containing pSV vectors were transfected into NSO cells in the following combinations (to produce antibodies having the indicated combinations of VH and VL regions):

MuVH/MuVK;
HuVH/HuVK;
HuVH/MuVK;
MuVH/HuVK;
HuVHA/HuVK;
HuVHT/HuVK;
HuVHT/HuVKF;
HuVH/HuVKVL;
HuVHS/HuVKVL;
HuVHSTAY/HuVK;
HuVH/HuVKF;
MuVH/HuVKF; and
HuVHSTAY/HuVKVL.

Combinations of the other VHs with the various VKs are expected to behave in an analogous manner, though having an unpredictable variation in degree of binding. Final selection of the optimum combination will be a function of obtaining an antibody having the best, selective antigen binding properties with the fewest murine amino acid substitutions.

The amino acid sequences of the initial humanized (CDR-grafted) COL-1 variable heavy ($V_H$) and variable light ($V_K$) regions, HuVH and HuVK, are show in FIGS. 1 and 2, respectively. NSO transfectants were screened for whole antibody expression and the antigen binding characteristics of the antibodies produced thereby were measured by an ELISA test against CEA. Results are presented in FIGS. 4–9. This data shows that—of the graft-humanized and the mix-and-match clones—MuVH/HuVK outperformed both HuVH/MuVK and HuVH/HuVK, but did not perform as well as the chimeric MuVH/MuVK antibodies.

These results indicate that the initial fully humanized antibody (HuVH/HuVK) exhibits a 20-fold loss in CEA antigen binding affinity. Thus, it exhibits about 5% the binding affinity of murine COL-1. Based on analysis of CEA binding of mix-and-match antibodies (HuVH/HuVK) and (MuVH/HuVK), it was determined that the reduction in CEA antigen binding was apparently largely attributable to the amino acid sequence of humanized heavy chain. However, an approximate 2-fold reduction in antigen binding also occurred apparently because of the amino acid sequence of the humanized kappa chain. This can be appreciated from the ELISA data in FIG. 4.

As a result of this research, a cell line which produces an antibody comprising the VHSTAY- and VKVL-containing heavy and light chains was deposited on Oct. 16, 1996 with the American Type Culture Collection, 10801 University Boulevard, Manassas, Va. 20110-2209 accorded Accession Number ATCC CRL-12208 (this is a murine plasmacytoma cell line). This deposit was made in accordance with the Budapest Treaty. This deposited cell line will be made irrevocably available, without restriction, upon issuance of a patent to this application, or any patent claiming benefit of priority to this application under 35 U.S.C. §120.

Based on the foregoing, it will be appreciated that the humanized antibodies disclosed herein exhibit antigen-binding characteristics, i.e., CEA affinities comparable to the parent monoclonal antibody, nCOL-1 (murine antibody), and to chimeric antibodies derived from nCOL-1, e.g., ChCOL-1γ1 (ATCC No. CRL 11217). Moreover, based on the foregoing results, these antibodies possess properties which will render them well suited for usage as in vivo diagnostics or therapeutics, e.g., improved serum clearance, metabolic properties, and little or no immunogenicity in humans.

These properties are highly significant because they will enable the subject humanized antibodies to be administered repeatedly, in large dosages, and over a prolonged period of time without significant adverse effects, e.g., a HAMA response or non-specific cytotoxicity. This is important for cancer treatment as well as for cancer diagnosis as it enables these antibodies to be used over prolonged time periods. Moreover, the clearance properties of the subject human antibodies will enable these antibodies to effectively target desired target sites, e.g., CEA expressing carcinomas (because of the effects of serum clearance on targeting efficiency). Therefore, the humanized antibodies of the present invention comprise a substantial improvement in relation to previously disclosed antibodies specific to CEA.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. Nucleic acid from which can be expressed either:
   A) a humanized antibody which specifically binds carcinoembryonic antigen ("CEA") wherein said humanized antibody comprises:
      1) at least one humanized VH having the amino acid sequence of any one of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12; and
      2) at least one humanized VL having the amino acid sequence of any one of SEQ ID NO:15, SEQ ID NO:16, and SEQ ID NO: 17; or
   B) a humanized antibody fragment thereof which specifically binds CEA.

2. A vector comprising nucleic acid according to claim 1.

3. The vector according to claim 2 wherein said vector is a bare nucleic acid segment, a carrier-associated nucleic acid segment, a nucleoprotein, a plasmid, a virus, a viroid, or a transposable element.

4. Nucleic acid according to claim 1 from which can be expressed either a humanized antibody having the amino acid sequence of the antibody expressed by a cell deposited as ATCC CRL-12208, or a humanized antibody fragment thereof.

5. The vector according to claim 2, said nucleic acid being that from which can be expressed either a humanized antibody having the amino acid sequence of the antibody expressed by a cell deposited as ATCC CRL-12208, or a humanized antibody fragment thereof.

* * * * *

SEQUENCE LISTING

```
<160> NUMBER OF SEQ ID NOS:  50

<210> SEQ ID NO 1
<211> LENGTH: 124
<212> TYPE: PRT
<213> ORGANISM: Mus musculus
<220> FEATURE:
<221> NAME/KEY: Murine Col-1 VH
<222> LOCATION: 1..124

<400> SEQUENCE: 1

Glu Val Gln Leu Gln Gln Ser Gly Ala Glu Leu Val Arg Ser Gly Ala
                 5                  10                  15

Ser Val Lys Met Ser Cys Thr Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Met Thr Thr Asp Tyr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Thr Arg Gly Leu Ser Thr Met Ile Thr Thr Arg Trp Phe Phe Asp
            100                 105                 110

Val Trp Gly Ala Gly Thr Thr Val Ala Val Ser Ser
        115                 120

<210> SEQ ID NO 2
<211> LENGTH: 124
<212> TYPE: PRT
<213> ORGANISM: Homo sapiens
<220> FEATURE:
<221> NAME/KEY: Human NEWM VH FR template
<222> LOCATION: 1..124
<223> OTHER INFORMATION: Amino acid sequence of the human framework
      regions fromthe NEWM antibody heavy chain variable region, with
      CDR2 and CDR3 amino acid residues depicted by Xaa
```

-continued

```
<400> SEQUENCE: 2

Gln Val Gln Leu Gln Glu Ser Gly Pro Gly Leu Val Arg Pro Ser Gln
                 5                  10                  15

Thr Leu Ser Leu Thr Cys Thr Val Ser Gly Phe Asn Ile Lys Asp Tyr
             20                  25                  30

Tyr Met His Trp Val Arg Gln Pro Pro Gly Arg Gly Leu Glu Trp Ile
         35                  40                  45

Gly Trp Ile Asp Pro Glu Asn Xaa Xaa Xaa Xaa Tyr Ala Pro Lys Phe
     50                  55                  60

Gln Gly Arg Val Thr Met Leu Val Asp Thr Ser Lys Asn Gln Phe Ser
 65                  70                  75                  80

Leu Arg Leu Ser Ser Val Thr Ala Ala Asp Thr Ala Val Tyr Xaa Xaa
                 85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Val Thr Val Ser Ser
        115                 120

<210> SEQ ID NO 3
<211> LENGTH: 124
<212> TYPE: PRT
<213> ORGANISM: Artificial Sequence
<220> FEATURE:
<221> NAME/KEY: Humanized COL-1 VH, HuVH
<222> LOCATION: 1..124
<223> OTHER INFORMATION: Humanized heavy chain variable region
      containing human NEWM VH FRs, murine COL-1 VH CDRs, and Phe-27,
      Asn-28, Ile-29, Lys-30, Asn-97, and Thr-98

<400> SEQUENCE: 3

Gln Val Gln Leu Gln Glu Ser Gly Pro Gly Leu Val Arg Pro Ser Gln
                 5                  10                  15

Thr Leu Ser Leu Thr Cys Thr Val Ser Gly Phe Asn Ile Lys Asp Tyr
             20                  25                  30

Tyr Met His Trp Val Arg Gln Pro Pro Gly Arg Gly Leu Glu Trp Ile
         35                  40                  45

Gly Trp Ile Asp Pro Glu Asn Gly Asp Thr Glu Tyr Ala Pro Lys Phe
     50                  55                  60

Gln Gly Arg Val Thr Met Leu Val Asp Thr Ser Lys Asn Gln Phe Ser
 65                  70                  75                  80

Leu Arg Leu Ser Ser Val Thr Ala Ala Asp Thr Ala Val Tyr Tyr Cys
                 85                  90                  95

Asn Thr Arg Gly Leu Ser Thr Met Ile Thr Thr Arg Trp Phe Phe Asp
            100                 105                 110

Val Trp Gly Gln Gly Ser Leu Val Thr Val Ser Ser
        115                 120

<210> SEQ ID NO 4
<211> LENGTH: 124
<212> TYPE: PRT
<213> ORGANISM: Artificial Sequence
<220> FEATURE:
<221> NAME/KEY: Humanized COL-1 VH, HuVHA
<222> LOCATION: 1..124
<223> OTHER INFORMATION: Humanized heavy chain variable region
      containing human NEWM VH FRs, murine COL-1 VH CDRs, and Ala-24,
      Phe-27, Asn-28, Ile-29, Lys-30, Asn-97, and Thr-98
```

<400> SEQUENCE: 4

Gln Val Gln Leu Gln Glu Ser Gly Pro Gly Leu Val Arg Pro Ser Gln
                 5                  10                  15
Thr Leu Ser Leu Thr Cys Thr Ala Ser Gly Phe Asn Ile Lys Asp Tyr
             20                  25                  30
Tyr Met His Trp Val Arg Gln Pro Pro Gly Arg Gly Leu Glu Trp Ile
         35                  40                  45
Gly Trp Ile Asp Pro Glu Asn Gly Asp Thr Glu Tyr Ala Pro Lys Phe
     50                  55                  60
Gln Gly Arg Val Thr Met Leu Val Asp Thr Ser Lys Asn Gln Phe Ser
 65                  70                  75                  80
Leu Arg Leu Ser Ser Val Thr Ala Ala Asp Thr Ala Val Tyr Tyr Cys
                 85                  90                  95
Asn Thr Arg Gly Leu Ser Thr Met Ile Thr Thr Arg Trp Phe Phe Asp
             100                 105                 110
Val Trp Gly Gln Gly Ser Leu Val Thr Val Ser Ser
         115                 120

<210> SEQ ID NO 5
<211> LENGTH: 124
<212> TYPE: PRT
<213> ORGANISM: Artificial Sequence
<220> FEATURE:
<221> NAME/KEY: Humanized COL-1 VH, HuVHAT
<222> LOCATION: 1..124
<223> OTHER INFORMATION: Humanized heavy chain variable region
      containing human NEWM VH FRs, murine COL-1 VH CDRs, and Ala-24,
      Phe-27, Asn-28, Ile-29, Lys-30, Thr-78, Asn-97, and Thr-98

<400> SEQUENCE: 5

Gln Val Gln Leu Gln Glu Ser Gly Pro Gly Leu Val Arg Pro Ser Gln
                 5                  10                  15
Thr Leu Ser Leu Thr Cys Thr Ala Ser Gly Phe Asn Ile Lys Asp Tyr
             20                  25                  30
Tyr Met His Trp Val Arg Gln Pro Pro Gly Arg Gly Leu Glu Trp Ile
         35                  40                  45
Gly Trp Ile Asp Pro Glu Asn Gly Asp Thr Glu Tyr Ala Pro Lys Phe
     50                  55                  60
Gln Gly Arg Val Thr Met Leu Val Asp Thr Ser Lys Asn Thr Phe Ser
 65                  70                  75                  80
Leu Arg Leu Ser Ser Val Thr Ala Ala Asp Thr Ala Val Tyr Tyr Cys
                 85                  90                  95
Asn Thr Arg Gly Leu Ser Thr Met Ile Thr Thr Arg Trp Phe Phe Asp
             100                 105                 110
Val Trp Gly Gln Gly Ser Leu Val Thr Val Ser Ser
         115                 120

<210> SEQ ID NO 6
<211> LENGTH: 124
<212> TYPE: PRT
<213> ORGANISM: Artificial Sequence
<220> FEATURE:
<221> NAME/KEY: Humanized COL-1 VH, HuVHAA
<222> LOCATION: 1..124
<223> OTHER INFORMATION: Humanized heavy chain variable region
      containing human NEWM VH FRs, murine COL-1 VH CDRs, and Ala-24,
      Phe-27, Asn-28, Ile-29, Lys-30, Ala-79, Asn-97, and Thr-98

<400> SEQUENCE: 6

Gln Val Gln Leu Gln Glu Ser Gly Pro Gly Leu Val Arg Pro Ser Gln
                5                   10                  15

Thr Leu Ser Leu Thr Cys Thr Ala Ser Gly Phe Asn Ile Lys Asp Tyr
            20                  25                  30

Tyr Met His Trp Val Arg Gln Pro Pro Gly Arg Gly Leu Glu Trp Ile
        35                  40                  45

Gly Trp Ile Asp Pro Glu Asn Gly Asp Thr Glu Tyr Ala Pro Lys Phe
    50                  55                  60

Gln Gly Arg Val Thr Met Leu Val Asp Thr Ser Lys Asn Gln Ala Ser
65                  70                  75                  80

Leu Arg Leu Ser Ser Val Thr Ala Ala Asp Thr Ala Val Tyr Tyr Cys
                85                  90                  95

Asn Thr Arg Gly Leu Ser Thr Met Ile Thr Thr Arg Trp Phe Phe Asp
            100                 105                 110

Val Trp Gly Gln Gly Ser Leu Val Thr Val Ser Ser
        115                 120

<210> SEQ ID NO 7
<211> LENGTH: 124
<212> TYPE: PRT
<213> ORGANISM: Artificial Sequence
<220> FEATURE:
<221> NAME/KEY: Humanized COL-1 VH, HuVHAY
<222> LOCATION: 1..124
<223> OTHER INFORMATION: Humanized heavy chain variable region
      containing human NEWM VH FRs, murine COL-1 VH CDRs, and Ala-24,
      Phe-27, Asn-28, Ile-29, Lys-30, Tyr-80, Asn-97, and Thr-98

<400> SEQUENCE: 7

Gln Val Gln Leu Gln Glu Ser Gly Pro Gly Leu Val Arg Pro Ser Gln
                5                   10                  15

Thr Leu Ser Leu Thr Cys Thr Ala Ser Gly Phe Asn Ile Lys Asp Tyr
            20                  25                  30

Tyr Met His Trp Val Arg Gln Pro Pro Gly Arg Gly Leu Glu Trp Ile
        35                  40                  45

Gly Trp Ile Asp Pro Glu Asn Gly Asp Thr Glu Tyr Ala Pro Lys Phe
    50                  55                  60

Gln Gly Arg Val Thr Met Leu Val Asp Thr Ser Lys Asn Gln Phe Tyr
65                  70                  75                  80

Leu Arg Leu Ser Ser Val Thr Ala Ala Asp Thr Ala Val Tyr Tyr Cys
                85                  90                  95

Asn Thr Arg Gly Leu Ser Thr Met Ile Thr Thr Arg Trp Phe Phe Asp
            100                 105                 110

Val Trp Gly Gln Gly Ser Leu Val Thr Val Ser Ser
        115                 120

<210> SEQ ID NO 8
<211> LENGTH: 124
<212> TYPE: PRT
<213> ORGANISM: Artificial Sequence
<220> FEATURE:
<221> NAME/KEY: Humanized COL-1 VH, HuVHATAY
<222> LOCATION: 1..124
<223> OTHER INFORMATION: Humanized heavy chain variable region
      containing human NEWM VH FRs, murine COL-1 VH CDRs, and Ala-24,
      Phe-27, Asn-28, Ile-29, Lys-30, Thr-78, Ala-79, Tyr-80, Asn-97,
      and Thr-98

<400> SEQUENCE: 8

Gln Val Gln Leu Gln Glu Gly Pro Gly Leu Val Arg Pro Ser Gln
                  5                  10                 15

Thr Leu Ser Leu Thr Cys Thr Ala Ser Gly Phe Asn Ile Lys Asp Tyr
             20                  25                  30

Tyr Met His Trp Val Arg Gln Pro Pro Gly Arg Gly Leu Glu Trp Ile
         35                  40                  45

Gly Trp Ile Asp Pro Glu Asn Gly Asp Thr Glu Tyr Ala Pro Lys Phe
     50                  55                  60

Gln Gly Arg Val Thr Met Leu Val Asp Thr Ser Lys Asn Thr Ala Tyr
 65                  70                  75                  80

Leu Arg Leu Ser Ser Val Thr Ala Ala Asp Thr Ala Val Tyr Tyr Cys
                 85                  90                  95

Asn Thr Arg Gly Leu Ser Thr Met Ile Thr Thr Arg Trp Phe Phe Asp
                100                 105                 110

Val Trp Gly Gln Gly Ser Leu Val Thr Val Ser Ser
            115                 120

<210> SEQ ID NO 9
<211> LENGTH: 124
<212> TYPE: PRT
<213> ORGANISM: Artificial Sequence
<220> FEATURE:
<221> NAME/KEY: Humanized COL-1 VH, HuVHASTAY
<222> LOCATION: 1..124
<223> OTHER INFORMATION: Humanized heavy chain variable region
      containing human NEWM VH FRs, murine COL-1 VH CDRs, and Ala-24,
      Phe-27, Asn-28, Ile-29, Lys-30, Ser-76, Thr-78, Ala-79, Tyr-80,
      Asn-97, and Thr-98

<400> SEQUENCE: 9

Gln Val Gln Leu Gln Glu Gly Pro Gly Leu Val Arg Pro Ser Gln
                  5                  10                 15

Thr Leu Ser Leu Thr Cys Thr Ala Ser Gly Phe Asn Ile Lys Asp Tyr
             20                  25                  30

Tyr Met His Trp Val Arg Gln Pro Pro Gly Arg Gly Leu Glu Trp Ile
         35                  40                  45

Gly Trp Ile Asp Pro Glu Asn Gly Asp Thr Glu Tyr Ala Pro Lys Phe
     50                  55                  60

Gln Gly Arg Val Thr Met Leu Val Asp Thr Ser Ser Asn Thr Ala Tyr
 65                  70                  75                  80

Leu Arg Leu Ser Ser Val Thr Ala Ala Asp Thr Ala Val Tyr Tyr Cys
                 85                  90                  95

Asn Thr Arg Gly Leu Ser Thr Met Ile Thr Thr Arg Trp Phe Phe Asp
                100                 105                 110

Val Trp Gly Gln Gly Ser Leu Val Thr Val Ser Ser
            115                 120

<210> SEQ ID NO 10
<211> LENGTH: 124
<212> TYPE: PRT
<213> ORGANISM: Artificial Sequence
<220> FEATURE:
<221> NAME/KEY: Humanized COL-1 VH, HuVHT
<222> LOCATION: 1..124
<223> OTHER INFORMATION: Humanized heavy chain variable region
      containing human NEWM VH FRs, murine COL-1 VH CDRs, and Phe-27,
      Asn-28, Ile-29, Lys-30, Thr-72, Asn-97, and Thr-98

-continued

```
<400> SEQUENCE: 10

Gln Val Gln Leu Gln Glu Gly Pro Gly Leu Val Arg Pro Ser Gln
                  5                  10                  15

Thr Leu Ser Leu Thr Cys Thr Val Ser Gly Phe Asn Ile Lys Asp Tyr
             20                  25                  30

Tyr Met His Trp Val Arg Gln Pro Pro Gly Arg Gly Leu Glu Trp Ile
         35                  40                  45

Gly Trp Ile Asp Pro Glu Asn Gly Asp Thr Glu Tyr Ala Pro Lys Phe
     50                  55                  60

Gln Gly Arg Val Thr Met Leu Thr Asp Thr Ser Lys Asn Gln Phe Ser
 65                  70                  75                  80

Leu Arg Leu Ser Ser Val Thr Ala Ala Asp Thr Ala Val Tyr Tyr Cys
                 85                  90                  95

Asn Thr Arg Gly Leu Ser Thr Met Ile Thr Thr Arg Trp Phe Phe Asp
             100                 105                 110

Val Trp Gly Gln Gly Ser Leu Val Thr Val Ser Ser
         115                 120

<210> SEQ ID NO 11
<211> LENGTH: 124
<212> TYPE: PRT
<213> ORGANISM: Artificial Sequence
<220> FEATURE:
<221> NAME/KEY: Humanized COL-1 VH, HuVHS
<222> LOCATION: 1..124
<223> OTHER INFORMATION: Humanized heavy chain variable region
      containing human NEWM VH FRs, murine COL-1 VH CDRs, and Phe-27,
      Asn-28, Ile-29, Lys-30, Ser-76, Asn-97, and Thr-98

<400> SEQUENCE: 11

Gln Val Gln Leu Gln Glu Gly Pro Gly Leu Val Arg Pro Ser Gln
                  5                  10                  15

Thr Leu Ser Leu Thr Cys Thr Val Ser Gly Phe Asn Ile Lys Asp Tyr
             20                  25                  30

Tyr Met His Trp Val Arg Gln Pro Pro Gly Arg Gly Leu Glu Trp Ile
         35                  40                  45

Gly Trp Ile Asp Pro Glu Asn Gly Asp Thr Glu Tyr Ala Pro Lys Phe
     50                  55                  60

Gln Gly Arg Val Thr Met Leu Val Asp Thr Ser Ser Asn Gln Phe Ser
 65                  70                  75                  80

Leu Arg Leu Ser Ser Val Thr Ala Ala Asp Thr Ala Val Tyr Tyr Cys
                 85                  90                  95

Asn Thr Arg Gly Leu Ser Thr Met Ile Thr Thr Arg Trp Phe Phe Asp
             100                 105                 110

Val Trp Gly Gln Gly Ser Leu Val Thr Val Ser Ser
         115                 120

<210> SEQ ID NO 12
<211> LENGTH: 124
<212> TYPE: PRT
<213> ORGANISM: Artificial Sequence
<220> FEATURE:
<221> NAME/KEY: Humanized COL-1 VH, HuVHSTAY
<222> LOCATION: 1..124
<223> OTHER INFORMATION: Humanized heavy chain variable region expressed
      from ATCC CRL-12208, and containing human NEWM VH FRs, murine
      COL-1 VH CDRs, and Phe-27, Asn-28, Ile-29, Lys-30, Ser-76, Thr-78,
      Ala-79, Tyr-80, Asn-97, and Thr-98
```

```
<400> SEQUENCE: 12

Gln Val Gln Leu Gln Glu Ser Gly Pro Gly Leu Val Arg Pro Ser Gln
                  5                  10                  15

Thr Leu Ser Leu Thr Cys Thr Val Ser Gly Phe Asn Ile Lys Asp Tyr
             20                  25                  30

Tyr Met His Trp Val Arg Gln Pro Pro Gly Arg Gly Leu Glu Trp Ile
         35                  40                  45

Gly Trp Ile Asp Pro Glu Asn Gly Asp Thr Glu Tyr Ala Pro Lys Phe
     50                  55                  60

Gln Gly Arg Val Thr Met Leu Val Asp Thr Ser Ser Asn Thr Ala Tyr
 65                  70                  75                  80

Leu Arg Leu Ser Ser Val Thr Ala Ala Asp Thr Ala Val Tyr Tyr Cys
                 85                  90                  95

Asn Thr Arg Gly Leu Ser Thr Met Ile Thr Thr Arg Trp Phe Phe Asp
            100                 105                 110

Val Trp Gly Gln Gly Ser Leu Val Thr Val Ser Ser
        115                 120

<210> SEQ ID NO 13
<211> LENGTH: 110
<212> TYPE: PRT
<213> ORGANISM: Mus musculus
<220> FEATURE:
<221> NAME/KEY: Murine COL-1 V(
<222> LOCATION: 1..110

<400> SEQUENCE: 13

Asp Ile Val Leu Thr Gln Ser Pro Ala Ser Leu Thr Val Ser Leu Gly
                  5                  10                  15

Leu Arg Ala Thr Ile Ser Cys Arg Ala Ser Lys Ser Val Ser Ala Ser
             20                  25                  30

Gly Tyr Ser Tyr Met His Trp Tyr Gln Gln Arg Pro Gly Gln Pro Pro
         35                  40                  45

Lys Leu Leu Ile Tyr Leu Ala Ser Asn Leu Gln Ser Gly Val Pro Ala
 50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Ser Arg
                 85                  90                  95

Glu Leu Pro Thr Phe Gly Gly Gly Thr Lys Leu Glu Ile Lys
            100                 105                 110

<210> SEQ ID NO 14
<211> LENGTH: 110
<212> TYPE: PRT
<213> ORGANISM: Homo sapiens
<220> FEATURE:
<221> NAME/KEY: Human REI V( FR template
<222> LOCATION: 1..110
<223> OTHER INFORMATION: Amino acid sequence of the human framework
      regions from the REI antibody light chain variable region, with
      CDR and carboxy-terminal amino acid residues depicted by Xaa

<400> SEQUENCE: 14

Asp Ile Gln Leu Thr Gln Ser Pro Ser Ser Leu Ser Ala Ser Val Gly
                  5                  10                  15

Asp Arg Val Thr Ile Thr Cys Arg Xaa Xaa Xaa Xaa Xaa Xaa Xaa Xaa
             20                  25                  30
```

```
Gly Tyr Ser Tyr Met His Trp Tyr Gln Gln Lys Pro Gly Lys Ala Pro
            35                  40                  45

Lys Leu Leu Ile Tyr Xaa Xaa Xaa Xaa Xaa Ser Gly Val Pro Ser
 50                  55                  60

Arg Phe Ser Gly Ser Gly Ser Gly Thr Asp Phe Thr Phe Thr Ile Ser
 65                  70                  75                  80

Ser Leu Gln Pro Glu Asp Ile Ala Thr Tyr Tyr Cys Gln Xaa Xaa Xaa
                 85                  90                  95

Xaa Xaa Xaa Thr Phe Gly Gln Gly Thr Lys Xaa Xaa Xaa Xaa
            100                 105                 110
```

<210> SEQ ID NO 15
<211> LENGTH: 110
<212> TYPE: PRT
<213> ORGANISM: Artificial Sequence
<220> FEATURE:
<221> NAME/KEY: Humanized COL-1 V(, HuVK
<222> LOCATION: 1..110
<223> OTHER INFORMATION: Humanized light chain variable region
      containing human REI V( FRs and murine COL-1 V( CDRs

<400> SEQUENCE: 15

```
Asp Ile Gln Met Thr Gln Ser Pro Ser Ser Leu Ser Ala Ser Val Gly
                 5                  10                  15

Asp Arg Val Thr Ile Thr Cys Arg Ala Ser Lys Ser Val Ser Ala Ser
             20                  25                  30

Gly Tyr Ser Tyr Met His Trp Tyr Gln Gln Thr Pro Gly Lys Ala Pro
            35                  40                  45

Lys Leu Leu Ile Tyr Leu Ala Ser Asn Leu Gln Ser Gly Val Pro Ser
 50                  55                  60

Arg Phe Ser Gly Ser Gly Ser Gly Thr Asp Tyr Thr Phe Thr Ile Ser
 65                  70                  75                  80

Ser Leu Gln Pro Glu Asp Ile Ala Thr Tyr Tyr Cys Gln His Ser Arg
                 85                  90                  95

Glu Leu Pro Thr Phe Gly Gln Gly Thr Lys Leu Gln Ile Thr
            100                 105                 110
```

<210> SEQ ID NO 16
<211> LENGTH: 110
<212> TYPE: PRT
<213> ORGANISM: Artificial Sequence
<220> FEATURE:
<221> NAME/KEY: Humanized COL-1 V(, HuVKVL
<222> LOCATION: 1..110
<223> OTHER INFORMATION: Humanized light chain variable region
      expressed from ATCC CRL-12208, and containing human REI V( FRs,
      murine COL-1 V( CDRs, and Val-3 and Leu-4

<400> SEQUENCE: 16

```
Asp Ile Val Leu Thr Gln Ser Pro Ser Ser Leu Ser Ala Ser Val Gly
                 5                  10                  15

Asp Arg Val Thr Ile Thr Cys Arg Ala Ser Lys Ser Val Ser Ala Ser
             20                  25                  30

Gly Tyr Ser Tyr Met His Trp Tyr Gln Gln Thr Pro Gly Lys Ala Pro
            35                  40                  45

Lys Leu Leu Ile Tyr Leu Ala Ser Asn Leu Gln Ser Gly Val Pro Ser
 50                  55                  60

Arg Phe Ser Gly Ser Gly Ser Gly Thr Asp Tyr Thr Phe Thr Ile Ser
 65                  70                  75                  80
```

```
Ser Leu Gln Pro Glu Asp Ile Ala Thr Tyr Tyr Cys Gln His Ser Arg
            85                  90                  95

Glu Leu Pro Thr Phe Gly Gln Gly Thr Lys Leu Gln Ile Thr
            100                 105                 110

<210> SEQ ID NO 17
<211> LENGTH: 110
<212> TYPE: PRT
<213> ORGANISM: Artificial Sequence
<220> FEATURE:
<221> NAME/KEY: Humanized COL-1 V(, HuVKF
<222> LOCATION: 1..110
<223> OTHER INFORMATION: Humanized light chain variable region
      containing human REI V( FRs, murine COL-1 V( CDRs, and Phe-75

<400> SEQUENCE: 17

Asp Ile Gln Met Thr Gln Ser Pro Ser Ser Leu Ser Ala Ser Val Gly
                5                   10                  15

Asp Arg Val Thr Ile Thr Cys Arg Ala Ser Lys Ser Val Ser Ala Ser
            20                  25                  30

Gly Tyr Ser Tyr Met His Trp Tyr Gln Gln Thr Pro Gly Lys Ala Pro
        35                  40                  45

Lys Leu Leu Ile Tyr Leu Ala Ser Asn Leu Gln Ser Gly Val Pro Ser
    50                  55                  60

Arg Phe Ser Gly Ser Gly Ser Gly Thr Asp Phe Thr Phe Thr Ile Ser
65                  70                  75                  80

Ser Leu Gln Pro Glu Asp Ile Ala Thr Tyr Tyr Cys Gln His Ser Arg
            85                  90                  95

Glu Leu Pro Thr Phe Gly Gln Gly Thr Lys Leu Gln Ile Thr
            100                 105                 110

<210> SEQ ID NO 18
<211> LENGTH: 348
<212> TYPE: DNA
<213> ORGANISM: Homo sapiens
<220> FEATURE:
<221> NAME/KEY: DNA template used to produce humanized COL-1 VH, HuVH
<222> LOCATION: 1..348
<223> OTHER INFORMATION: DNA encoding human NEWM heavy chain variable
      region FRs and murine COL-1 VH CDR1, with CDR2 and CDR3 amino acid
      residue-encoding codons depicted by NNN

<400> SEQUENCE: 18 cag gtc caa ctg cag gag agc ggt cca ggt ctt gtg aga cct agc cag     48
Gln Val Gln Leu Gln Glu Ser Gly Pro Gly Leu Val Arg Pro Ser Gln
                5                   10                  15 acc ctg agc ctg acc tgc acc gtg tct ggc ttc aac att aaa gac tac     96
Thr Leu Ser Leu Thr Cys Thr Val Ser Gly Phe Asn Ile Lys Asp Tyr
            20                  25                  30 tat atg cac tgg gtg aga cag cca cct gga cga ggt ctt gag tgg att    144
Tyr Met His Trp Val Arg Gln Pro Pro Gly Arg Gly Leu Glu Trp Ile
        35                  40                  45 gga tgg att gat cct gag aat nnn nnn nnn nnn tat gcc ccg aag ttc    192
Gly Trp Ile Asp Pro Glu Asn Xaa Xaa Xaa Xaa Tyr Ala Pro Lys Phe
    50                  55                  60 cag ggc aga gtg aca atg ctg gta gac acc agc aag aac cag ttc agc    240
Gln Gly Arg Val Thr Met Leu Val Asp Thr Ser Lys Asn Gln Phe Ser
65                  70                  75                  80 ctg aga ctc agc agc gtg aca gcc gcc gac acc gcg gtc tat nnn nnn    288
Leu Arg Leu Ser Ser Val Thr Ala Ala Asp Thr Ala Val Tyr Xaa Xaa
            85                  90                  95
```

-continued

```
nnn nnn nnn nnn nnn nnn nnn nnn nnn nnn nnn nnn nnn nnn gtc      336
Xaa Xaa Xaa Xaa Xaa Xaa Xaa Xaa Xaa Xaa Xaa Xaa Xaa Xaa Val
            100                 105                 110 acc gtc tcc tca                                                  348
Thr Val Ser Ser
        115

<210> SEQ ID NO 19
<211> LENGTH: 372
<212> TYPE: DNA
<213> ORGANISM: Artificial Sequence
<220> FEATURE:
<221> NAME/KEY: DNA template used to produce HuVHT, HuVHS, and HuVHA
<222> LOCATION: 1..372
<223> OTHER INFORMATION: DNA encoding the humanized heavy chain variable
      region, HuVH, containing human NEWM VH FRs, murine COL-1 VH CDRs,
      and Phe-27, Asn-28, Ile-29, Lys-30, Asn-97, and Thr-98

<400> SEQUENCE: 19 cag gtc caa ctg cag gag agc ggt cca ggt ctt gtg aga cct agc cag   48
Gln Val Gln Leu Gln Glu Ser Gly Pro Gly Leu Val Arg Pro Ser Gln
                5                   10                  15 acc ctg agc ctg acc tgc acc gtg tct ggc ttc aac att aaa gac tac   96
Thr Leu Ser Leu Thr Cys Thr Val Ser Gly Phe Asn Ile Lys Asp Tyr
            20                  25                  30 tat atg cac tgg gtg aga cag cca cct gga cga ggt ctt gag tgg att  144
Tyr Met His Trp Val Arg Gln Pro Pro Gly Arg Gly Leu Glu Trp Ile
        35                  40                  45 gga tgg att gat cct gag aat ggt gat act gaa tat gcc ccg aag ttc  192
Gly Trp Ile Asp Pro Glu Asn Gly Asp Thr Glu Tyr Ala Pro Lys Phe
    50                  55                  60 cag ggc aga gtg aca atg ctg gta gac acc agc aag aac cag ttc agc  240
Gln Gly Arg Val Thr Met Leu Val Asp Thr Ser Lys Asn Gln Phe Ser
65                  70                  75                  80 ctg aga ctc agc agc gtg aca gcc gcc gac acc gcg gtc tat tac tgt  288
Leu Arg Leu Ser Ser Val Thr Ala Ala Asp Thr Ala Val Tyr Tyr Cys
                85                  90                  95 aat aca cgg ggt cta tct act atg att acg acg cgt tgg ttc ttc gat  336
Asn Thr Arg Gly Leu Ser Thr Met Ile Thr Thr Arg Trp Phe Phe Asp
            100                 105                 110 gtc tgg ggc caa ggg tcc ttg gtc acc gtc tcc tca                  372
Val Trp Gly Gln Gly Ser Leu Val Thr Val Ser Ser
        115                 120

<210> SEQ ID NO 20
<211> LENGTH: 318
<212> TYPE: DNA
<213> ORGANISM: Homo sapiens
<220> FEATURE:
<221> NAME/KEY: DNA template used to produce the humanized COL-1 VK,
      HuVK
<222> LOCATION: 1..318
<223> OTHER INFORMATION: DNA encoding human REI light chain variable
      region FRs, with CDR amino acid residue-encoding codons depicted
      by NNN

<400> SEQUENCE: 20 gac atc car ctg acc cag agc cca agc agc ctg agc gcc agc gtg ggt   48
Asp Ile Gln Leu Thr Gln Ser Pro Ser Ser Leu Ser Ala Ser Val Gly
                5                   10                  15 gac aga gtg acc atc acc tgt agg nnn nnn nnn nnn nnn nnn nnn nnn   96
Asp Arg Val Thr Ile Thr Cys Arg Xaa Xaa Xaa Xaa Xaa Xaa Xaa Xaa
            20                  25                  30
```

```
ggc tat agt tat atg cac tgg tac cag cag acg cca ggt aag gct cca    144
Gly Tyr Ser Tyr Met His Trp Tyr Gln Gln Thr Pro Gly Lys Ala Pro
        35                  40                  45 aag ctg ctg atc tac nnn nnn nnn nnn nnn tct ggt gtg cca agc        192
Lys Leu Leu Ile Tyr Xaa Xaa Xaa Xaa Xaa Ser Gly Val Pro Ser
 50                  55                  60 aga ttc agc ggt agc ggt agc ggt acc gac tty acc ttc acc atc agc    240
Arg Phe Ser Gly Ser Gly Ser Gly Thr Asp Phe

```
<210> SEQ ID NO 23
<211> LENGTH: 16
<212> TYPE: DNA
<213> ORGANISM: Artificial Sequence
<220> FEATURE:
<221> NAME/KEY: Oligonucleotide 11
<222> LOCATION: 1..16
<223> OTHER INFORMATION: DNA sequence of oligonucleotide primer for PCR
      amplification of heavy chain variable regions

<400> SEQUENCE: 23
aacagctatg accatg                                                    16

<210> SEQ ID NO 24
<211> LENGTH: 22
<212> TYPE: DNA
<213> ORGANISM: Artificial Sequence
<220> FEATURE:
<221> NAME/KEY: Oligonucleotide 385
<222> LOCATION: 1..22
<223> OTHER INFORMATION: DNA sequence of oligonucleotide primer for PCR
      amplification of light chain variable regions

<400> SEQUENCE: 24
gcgggcctct tcgctattac gc                                             22

<210> SEQ ID NO 25
<211> LENGTH: 22
<212> TYPE: DNA
<213> ORGANISM: Artificial Sequence
<220> FEATURE:
<221> NAME/KEY: Oligonucleotide 391
<222> LOCATION: 1..22
<223> OTHER INFORMATION: DNA sequence of oligonucleotide primer for PCR
      amplification of heavy chain variable regions

<400> SEQUENCE: 25
ctctctcagg gccaggcggt ga                                             22

<210> SEQ ID NO 26
<211> LENGTH: 32
<212> TYPE: DNA
<213> ORGANISM: Artificial Sequence
<220> FEATURE:
<221> NAME/KEY: Oligonucleotide 836
<222> LOCATION: 1..32
<223> OTHER INFORMATION: DNA sequence of mutagenic oligonucleotide for
      production of DNA encoding the humanized COL-1 heavy chain
      variable region, HuVH

<400> SEQUENCE: 26
tgagaatggt gatactgaat atgccccgaa gt                                  32

<210> SEQ ID NO 27
<211> LENGTH: 34
<212> TYPE: DNA
<213> ORGANISM: Artificial Sequence
<220> FEATURE:
<221> NAME/KEY: Oligonucleotide 837
<222> LOCATION: 1..34
<223> OTHER INFORMATION: DNA sequence of mutagenic oligonucleotide for
      production of DNA encoding the humanized COL-1 heavy chain
      variable region, HuVH

<400> SEQUENCE: 27
tcggggcata ttcagtatca ccattctcag gatc                                34

<210> SEQ ID NO 28
<211> LENGTH: 59
```

<210> SEQ ID NO 28
<211> LENGTH: 59 (implied)
<212> TYPE: DNA
<213> ORGANISM: Artificial Sequence
<220> FEATURE:
<221> NAME/KEY: Oligonucleotide 838
<222> LOCATION: 1..59
<223> OTHER INFORMATION: DNA sequence of mutagenic oligonucleotide for
      production of DNA encoding the humanized COL-1 heavy chain
      variable region, HuVH

<400> SEQUENCE: 28
actatgatta cgacgcgttg gttcttcgat gtctggggcc aagggtcctt ggtcacgtc      59

<210> SEQ ID NO 29
<211> LENGTH: 55
<212> TYPE: DNA
<213> ORGANISM: Artificial Sequence
<220> FEATURE:
<221> NAME/KEY: Oligonucleotide 839
<222> LOCATION: 1..55
<223> OTHER INFORMATION: DNA sequence of mutagenic oligonucleotide for
      production of DNA encoding the humanized COL-1 heavy chain
      variable region, HuVH

<400> SEQUENCE: 29
acgcgtcgta atcatagtag atagaccccg tgtattacag taatagaccg cggtg          55

<210> SEQ ID NO 30
<211> LENGTH: 44
<212> TYPE: DNA
<213> ORGANISM: Artificial Sequence
<220> FEATURE:
<221> NAME/KEY: Oligonucleotide 842
<222> LOCATION: 1..44
<223> OTHER INFORMATION: DNA sequence of mutagenic oligonucleotide for
      production of DNA encoding the humanized COL-1 light chain
      variable regions, HuV( and HuVKF

<400> SEQUENCE: 30
tatagccaga tgcactgaca cttttgctgg ccctacaggt gatg                      44

<210> SEQ ID NO 31
<211> LENGTH: 23
<212> TYPE: DNA
<213> ORGANISM: Artificial Sequence
<220> FEATURE:
<221> NAME/KEY: Oligonucleotide 844
<222> LOCATION: 1..23
<223> OTHER INFORMATION: DNA sequence of mutagenic oligonucleotide for
      production of DNA encoding the humanized COL-1 light chain
      variable region, HuV(

<400> SEQUENCE: 31
gctctgggtc atctggatgt cgg                                             23

<210> SEQ ID NO 32
<211> LENGTH: 72
<212> TYPE: DNA
<213> ORGANISM: Artificial Sequence
<220> FEATURE:
<221> NAME/KEY: Oligonucleotide 849
<222> LOCATION: 1..72
<223> OTHER INFORMATION: DNA sequence of mutagenic oligonucleotide for
      production of DNA encoding the humanized COL-1 light chain
      variable region, HuV(

<400> SEQUENCE: 32
ttctactcac gtgtgatttg cagcttggtc ccttggccga acgtaggaag ctccctactg     60
tgctggcagt ag                                                         72

<210> SEQ ID NO 33
<211> LENGTH: 25
<212> TYPE: DNA
<213> ORGANISM: Artificial Sequence
<220> FEATURE:
<221> NAME/KEY: Oligonucleotide 850
<222> LOCATION: 1..25
<223> OTHER INFORMATION: DNA sequence of mutagenic oligonucleotide for
      production of DNA encoding the humanized COL-1 light chain
      variable region, HuV(

<400> SEQUENCE: 33
atggtgaagg tgtagtcggt accgc                                       25

<210> SEQ ID NO 34
<211> LENGTH: 25
<212> TYPE: DNA
<213> ORGANISM: Artificial Sequence
<220> FEATURE:
<221> NAME/KEY: Oligonucleotide 851
<222> LOCATION: 1..25
<223> OTHER INFORMATION: DNA sequence of mutagenic oligonucleotide for
      production of DNA encoding the humanized COL-1 light chain
      variable region, HuV(

<400> SEQUENCE: 34
gccttacctg gcgtctgctg gtacc                                       25

<210> SEQ ID NO 35
<211> LENGTH: 29
<212> TYPE: DNA
<213> ORGANISM: Artificial Sequence
<220> FEATURE:
<221> NAME/KEY: Oligonucleotide 841
<222> LOCATION: 1..29
<223> OTHER INFORMATION: DNA sequence of mutagenic oligonucleotide for
      production of DNA encoding the humanized COL-1 light chain
      variable region, HuV(

<400> SEQUENCE: 35
gcacaccaga ttgtaggttg gatgcaagg                                   29

<210> SEQ ID NO 36
<211> LENGTH: 24
<212> TYPE: DNA
<213> ORGANISM: Artificial Sequence
<220> FEATURE:
<221> NAME/KEY: Oligonucleotide 954
<222> LOCATION: 1..24
<223> OTHER INFORMATION: DNA sequence of mutagenic oligonucleotide for
      production of DNA encoding the humanized COL-1 heavy chain
      variable region, HuVHT

<400> SEQUENCE: 36
gacaatgctg acagacacca gcaa                                        24

<210> SEQ ID NO 37
<211> LENGTH: 24
<212> TYPE: DNA
<213> ORGANISM: Artificial Sequence
<220> FEATURE:
<221> NAME/KEY: Oligonucleotide 955
<222> LOCATION: 1..24
<223> OTHER INFORMATION: DNA sequence of mutagenic oligonucleotide for
      production of DNA encoding the humanized COL-1 heavy chain
      variable region, HuVHT

<400> SEQUENCE: 37
tgctggtgtc tgtcagcatt gtca                                        24

<210> SEQ ID NO 38
<211> LENGTH: 21
<212> TYPE: DNA
<213> ORGANISM: Artificial Sequence
<220> FEATURE:
<221> NAME/KEY: Oligonucleotide 684
<222> LOCATION: 1..21
<223> OTHER INFORMATION: DNA sequence of mutagenic oligonucleotide for
      production of DNA encoding the humanized COL-1 heavy chain
      variable region, HuVHS

<400> SEQUENCE: 38
caccagcagc aaccagttca g                                             21

<210> SEQ ID NO 39
<211> LENGTH: 21
<212> TYPE: DNA
<213> ORGANISM: Artificial Sequence
<220> FEATURE:
<221> NAME/KEY: Oligonucleotide 683
<222> LOCATION: 1..21
<223> OTHER INFORMATION: DNA sequence of mutagenic oligonucleotide for
      production of DNA encoding the humanized COL-1 heavy chain
      variable region, HuVHS

<400> SEQUENCE: 39
actggttgct cgtggtctct a                                             21

<210> SEQ ID NO 40
<211> LENGTH: 35
<212> TYPE: DNA
<213> ORGANISM: Artificial Sequence
<220> FEATURE:
<221> NAME/KEY: Oligonucleotide 1026
<222> LOCATION: 1..35
<223> OTHER INFORMATION: DNA sequence of mutagenic oligonucleotide for
      production of DNA encoding the humanized COL-1 heavy chain
      variable region, HuVHSTAY

<400> SEQUENCE: 40
accagcagca acacagccta cctgagactc agcag                              35

<210> SEQ ID NO 41
<211> LENGTH: 36
<212> TYPE: DNA
<213> ORGANISM: Artificial Sequence
<220> FEATURE:
<221> NAME/KEY: Oligonucleotide 1028
<222> LOCATION: 1..36
<223> OTHER INFORMATION: DNA sequence of mutagenic oligonucleotide for
      production of DNA encoding the humanized COL-1 heavy chain
      variable region, HuVHSTAY

<400> SEQUENCE: 41
tgctgagtct caggtaggct gtgttgctgc tggtgt                             36

<210> SEQ ID NO 42
<211> LENGTH: 26
<212> TYPE: DNA
<213> ORGANISM: Artificial Sequence
<220> FEATURE:
<221> NAME/KEY: Oligonucleotide 745
<222> LOCATION: 1..26
<223> OTHER INFORMATION: DNA sequence of mutagenic oligonucleotide for
      production of DNA encoding the humanized COL-1 heavy chain
      variable region, HuVHA

<400> SEQUENCE: 42
tgacctgcac cgcgtctggc ttcaac                                        26

```
<210> SEQ ID NO 43
<211> LENGTH: 26
<212> TYPE: DNA
<213> ORGANISM: Artificial Sequence
<220> FEATURE:
<221> NAME/KEY: Oligonucleotide 746
<222> LOCATION: 1..26
<223> OTHER INFORMATION: DNA sequence of mutagenic oligonucleotide for
      production of DNA encoding the humanized COL-1 heavy chain
      variable region, HuVHA

<400> SEQUENCE: 43
ttgaagccag acgcggtgca ggtcag                                            26

<210> SEQ ID NO 44
<211> LENGTH: 20
<212> TYPE: DNA
<213> ORGANISM: Artificial Sequence
<220> FEATURE:
<221> NAME/KEY: Oligonucleotide 1071
<222> LOCATION: 1..20
<223> OTHER INFORMATION: DNA sequence of mutagenic oligonucleotide for
      production of DNA encoding the humanized COL-1 heavy chain
      variable region, HuVHAA

<400> SEQUENCE: 44
gagactcagc agcgtgacag                                                   20

<210> SEQ ID NO 45
<211> LENGTH: 40
<212> TYPE: DNA
<213> ORGANISM: Artificial Sequence
<220> FEATURE:
<221> NAME/KEY: Oligonucleotide 1072
<222> LOCATION: 1..40
<223> OTHER INFORMATION: DNA sequence of mutagenic oligonucleotide for
      production of DNA encoding the humanized COL-1 heavy chain
      variable region, HuVHAA

<400> SEQUENCE: 45
cgctgctgag tctcaggctg aatgtgttct tgctggtgtc                             40

<210> SEQ ID NO 46
<211> LENGTH: 38
<212> TYPE: DNA
<213> ORGANISM: Artificial Sequence
<220> FEATURE:
<221> NAME/KEY: Oligonucleotide 1074
<222> LOCATION: 1..38
<223> OTHER INFORMATION: DNA sequence of mutagenic oligonucleotide for
      production of DNA encoding the humanized COL-1 heavy chain
      variable region, HuVHAT

<400> SEQUENCE: 46
cgctgctgag tctcaggctg gcctggttct tgctggtg                               38

<210> SEQ ID NO 47
<211> LENGTH: 33
<212> TYPE: DNA
<213> ORGANISM: Artificial Sequence
<220> FEATURE:
<221> NAME/KEY: Oligonucleotide 1073
<222> LOCATION: 1..33
<223> OTHER INFORMATION: DNA sequence of mutagenic oligonucleotide for
      production of DNA encoding the humanized COL-1 heavy chain
      variable region, HuVHAY

<400> SEQUENCE: 47
cgctgctgag tctcaggtag aactggttct tgc                                    33
```

```
<210> SEQ ID NO 48
<211> LENGTH: 40
<212> TYPE: DNA
<213> ORGANISM: Artificial Sequence
<220> FEATURE:
<221> NAME/KEY: Oligonucleotide 1075
<222> LOCATION: 1..40
<223> OTHER INFORMATION: DNA sequence of mutagenic oligonucleotide for
      production of DNA encoding the humanized COL-1 heavy chain
      variable region, HuVHATAY

<400> SEQUENCE: 48
cgctgctgag tctcaggtag gctgtgttct tgctggtgtc                           40

<210> SEQ ID NO 49
<211> LENGTH: 25
<212> TYPE: DNA
<213> ORGANISM: Artificial Sequence
<220> FEATURE:
<221> NAME/KEY: Oligonucleotide 1010
<222> LOCATION: 1..25
<223> OTHER INFORMATION: DNA sequence of mutagenic oligonucleotide for
      production of DNA encoding the humanized COL-1 light chain
      variable region, HuVKVL

<400> SEQUENCE: 49
actccgacat cgtgctgacc cagag                                           25

<210> SEQ ID NO 50
<211> LENGTH: 24
<212> TYPE: DNA
<213> ORGANISM: Artificial Sequence
<220> FEATURE:
<221> NAME/KEY: Oligonucleotide 1011
<222> LOCATION: 1..24
<223> OTHER INFORMATION: DNA sequence of mutagenic oligonucleotide for
      production of DNA encoding the humanized COL-1 light chain
      variable region, HuVKVL

<400> SEQUENCE: 50
ctctgggtca gcacgatgtc ggag                                            24
```